US006486341B1

(12) United States Patent
Ziegler

(10) Patent No.: US 6,486,341 B1
(45) Date of Patent: Nov. 26, 2002

(54) N-ALKOXY-N-PHENYLCARBAMATE DERIVATIVES

(75) Inventor: Hugo Ziegler, Witterswil (CH)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/889,024

(22) PCT Filed: Jan. 14, 2000

(86) PCT No.: PCT/EP00/00266

§ 371 (c)(1),
(2), (4) Date: Jul. 10, 2001

(87) PCT Pub. No.: WO00/41476

PCT Pub. Date: Jul. 20, 2000

(30) Foreign Application Priority Data

Jan. 15, 1999 (CH) .................................... 68/99

(51) Int. Cl.$^7$ .................... C07C 261/00; C07C 239/00; A01N 43/46; A01N 43/40
(52) U.S. Cl. ........................ 560/24; 560/29; 560/30; 560/312; 514/274; 514/345; 514/478; 514/485
(58) Field of Search ..................... 560/29, 30, 24, 560/312; 514/274, 345, 485, 478

(56) References Cited

U.S. PATENT DOCUMENTS

| 5,824,705 A | * 10/1998 | Mueller et al. ............. 514/485 |
| 5,981,532 A | 11/1999 | Mueller et al. ............. 514/256 |
| 6,075,148 A | * 6/2000 | Mueller et al. ............. 546/334 |
| 6,252,083 B1 | * 6/2001 | Mueller et al. ............. 546/334 |

FOREIGN PATENT DOCUMENTS

WO 97/16415 5/1997

OTHER PUBLICATIONS

PCT EP00/00266, International Search Report.*
*Patent Abstracts of Japan, vol. 1998, No. 5, Apr. 30, 1998 & JP 10025271.

Russian Journal of Inorganic Chemistry, vol. 11, No. 1, Jan. 1966, pp. 39–41, A.V. Ablov, L.F. Chapurina and N.I. Belichuk, Infrared Absorption Spectra of Metal Derivatives of 3–Hydra–Zonobutan–2–One Oxime.
Chem. Ber, 58, (monh unavailable) 1925, p. 1240, Neber, Hartung, Ruopp: Die steroisomeren.
Journal of Chem. Soc., (month unavailable) 1951, pp. 1929–1931, H.C. Barany, E.A. Braude, and M. Pianka, "Some Derivatives of Diacetyl".
Tetrahedron, vol. 44, No. 1, (month unavailable) 1988, pp. 147–162, Derek H.R. Barton, Gerorge Bashiardes and Jean–Louis Fourrey, Studies on the Oxidation of Hydrazones with Iodine and with Phenylselenenyl Bromide in the Presence of Strong Organic Bases; An Improved Procedure for the Synthesis of Vinyl Iodies and Phenyl–Vinyl Selenides.
Liebigs Annalen der Chemie, GE, Nov. 1989, pp. 1071–1074, Horst Gnichtel und Bernhard Töpper, Die Konfiguration der 1,2–Diketon–hydrazon–oxime.
Journal of American Chem. Soc., vol. 83, Oct.–Dec. 1961, pp. 4262–4267, Henry Rapoport and William Nilsson, The Wolff–Kishner Reaction with α–Oximinoketones Chem. Ber., 34, (month unavailable) 1901, pp. 3788–3793, Otto Buhlmann und Alfred Einhorn: Zur Kenntniss des Anthranils.

* cited by examiner

Primary Examiner—Alan L. Rotman
Assistant Examiner—Héctor Reyes
(74) Attorney, Agent, or Firm—Joseph C. Gil

(57) ABSTRACT

Compounds of formula (I) wherein $R_1$ is $C_1$–$C_4$-alkyl or cyclopropyl; $R_2$ is $C_1$–$C_6$-alkyl, $C_2$–$C_6$-alkenyl, $C_2$–$C_6$-alkinyl; or $C_1$–$C_6$-alkyl substituted by 1 to 5 fluorine atoms; $R_3$ is $C_1$–$C_6$-alkyl, $C_1$–$C_6$-alkoxy, $C_3$–$C_6$-cycloalkyl, $C_3$–$C_6$-cycloalkoxy, $C_2$–$C_6$-alkenyl, $C_2$–$C_6$-alkenyloxy, $C_2$–$C_6$-alkinyl, $C_2$–$C_6$-alkinyloxy, $C_1$–$C_6$-alkoxycarbonyl, CN, or aryl, heteroaryl, heterocyclyl, aryloxy, heteroaryloxy or heterocyclyloxy, whereby the above-mentioned groups may be substituted by identical of different substituents, $R_5$ signifies hydrogen or methyl; $R_6$ and $R_7$ are $C_1$–$C_4$-alkyl; have microbicidal, insecticidal and acaricidal activity and may be used for the control of pests and plant-pathogenic fungi in agriculture, horticulture and in the field of hygiene.

20 Claims, No Drawings

N-ALKOXY-N-PHENYLCARBAMATE DERIVATIVES

FIELD OF THE INVENTION

The present invention relates to new N-alkoxy-N-phenylcarbamates having microbicidal, insecticidal and acaricidal activity, a process for their preparation, new intermediates for the preparation thereof, agrochemical compositions containing these active ingredients, as well as the use thereof in the control and prevention of plant-pathogenic fungi, acarids and insects in agriculture and in the field of hygiene.

DETAILED DESCRIPTION

The new N-alkoxy-N-phenylcarbamates fall within formula I,

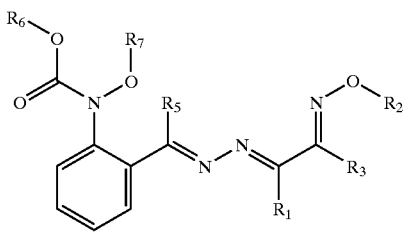

wherein:
- $R_1$ is $C_1$–$C_4$-alkyl or cyclopropyl;
- $R_2$ is $C_1$–$C_6$-alkyl, $C_2$–$C_6$-alkenyl, $C_2$–$C_6$-alkinyl; or $C_1$–$C_6$-alkyl substituted by 1 to 5 fluorine atoms;
- $R_3$ is $C_1$–$C_6$-alkyl, $C_1$–$C_6$-alkoxy, $C_3$–$C_6$-cycloalkyl, $C_3$–$C_6$-cycloalkoxy, $C_2$–$C_6$-alkenyl, $C_2$–$C_6$-alkenyloxy, $C_2$–$C_6$-alkinyl, $C_2$–$C_6$-alkinyloxy, $C_1$–$C_6$-alkoxycarbonyl or CN, whereby, with the exception of CN, the above-mentioned groups may be substituted by one or more identical or different substituents selected from the group comprising halogen, cyano, nitro, $C_1$–$C_6$-alkoxycarbonyl, $C_1$–$C_6$-alkoxy, $C_1$–$C_6$-alkylthio, aminocarbonyl, $C_1$–$C_6$-alkylaminocarbonyl, di-$C_1$–$C_6$-alkylaminocarbonyl, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, heteroaryl, heteroaryloxy, whereby the cyclic radicals in turn may be substituted by one or more identical or different substituents selected from the group comprising halogen, cyano, nitro, $C_1$–$C_6$-alkyl, $C_1$–$C_6$-halogenalkyl, $C_1$–$C_6$-alkoxy, $C_1$–$C_6$-halogenalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, optionally substituted benzyl, optionally substituted benzyloxy, optionally substituted aryl, optionally substituted aryloxy, optionally substituted heteroaryl and optionally substituted heteroaryloxy; whereby the above-mentioned aromatic groups may be substituted by one or more identical or different substituents selected from the group comprising halogen, cyano, nitro, $C_1$–$C_6$-alkyl, $C_1$–$C_6$-halogenalkyl, $C_1$–$C_6$-alkoxy, $C_1$–$C_6$-halogenalkoxy, $C_1$–$C_6$-alkoxycarbonyl, $C_1$–$C_6$-alkylthio, $C_1$–$C_6$-alkylamino, di-$C_1$–$C_6$-alkylamino and $C_2$–$C_6$-alkenyl; or
- $R_3$ signifies aryl, heteroaryl, heterocyclyl, aryloxy, heteroaryloxy or heterocyclyloxy, whereby the above-mentioned groups may be substituted by one or more identical or different substituents selected from the group comprising halogen, $C_1$–$C_6$-alkyl, $C_1$–$C_6$-alkoxy, halogen-$C_1$–$C_6$-alkoxy, halogen-$C_1$–$C_6$-alkyl, $C_1$–$C_6$-alkylthio, halogen-$C_1$–$C_6$-alkylthio, $C_1$–$C_6$-alkylsulfinyl, halogen-$C_1$–$C_6$-alkylsulfinyl, $C_1$–$C_6$-alkylsulfonyl, halogen-$C_1$–$C_6$-alkylsulfonyl, $C_2$–$C_6$-alkenyl, $C_2$–$C_6$-alkenyloxy, $C_2$–$C_6$-alkinyl, $C_3$–$C_6$-alkinyloxy, $C_1$–$C_6$-alkylcarbonyl, halogen-$C_1$–$C_6$-alkylcarbonyl, $C_1$–$C_6$-alkoxycarbonyl, halogen-$C_1$–$C_6$-alkoxycarbonyl, $C_1$–$C_6$-alkylaminocarbonyl, di-($C_1$–$C_6$-alkyl)-aminocarbonyl, whereby the alkyl groups may be identical or different, $C_1$–$C_6$-alkylaminothiocarbonyl, di-($C_1$–$C_6$-alkyl)-aminothiocarbonyl, whereby the alkyl groups may be identical or different, $C_1$–$C_6$-alkylamino, di-($C_1$–$C_6$-alkyl)-amino, $NO_2$, an unsubstituted $C_1$–$C_4$-alkylenedioxy group or one which is mono- to tetrasubstituted by $C_1$–$C_4$-alkyl and/or by halogen; or CN, $SF_5$, OH and $QR_4$;
- Q signifies a direct bond, O, O($C_1$–$C_6$-alkylene), ($C_1$–$C_6$-alkylene)O, S(=O)p, S(=O)p($C_1$–$C_6$-alkylene), ($C_1$–$C_6$-alkylene)S(=O)p, $C_1$–$C_8$-alkylene, $C_2$–$C_6$-alkenylene or $C_2$–$C_6$-alkinylene;
- $R_4$ signifies an unsubstituted $C_2$–$C_6$-alkenyl- or $C_2$–$C_6$-alkinyl group or one which is substituted by 1 to 3 halogen atoms, a ($C_1$–$C_4$-alkyl)$_3$Si group, whereby the alkyl groups may be identical or different, CN, an unsubstituted or mono- to penta-substituted $C_3$–$C_6$-cycloalkyl, aryl, heteroaryl or heterocyclyl group, whereby the substituents are selected from the group comprising halogen, $C_1$–$C_6$-alkyl, halogen-$C_1$–$C_6$-alkyl, $C_1$–$C_6$-alkoxy, halogen-$C_1$–$C_6$-alkoxy, phenoxy, CN, $SF_5$, $NO_2$, $C_1$–$C_6$-alkylsulfinyl, halogen-$C_1$–$C_6$-alkylsulfinyl, $C_1$–$C_6$-alkylsulfonyl, halogen-$C_1$–$C_6$-alkylsulfonyl and $C_1$–$C_4$-alkylenedioxy, the latter being unsubstituted or mono- to tetrasubstituted by $C_1$–$C_4$-alkyl and/or by halogen;
- p is 0, 1 or 2;
- $R_5$ signifies hydrogen or methyl;
- $R_6$ and $R_7$ are $C_1$–$C_4$-alkyl;

According to the present application, formula I includes all isomeric forms and mixtures thereof, e.g. racemic mixtures and any [E/Z] mixtures. Alkyl—as a group per se and as a structural element of other groups and compounds, such as of halogenalkyl, alkoxy and alkylthio—is either straight-chained, i.e. methyl, ethyl, propyl, butyl, pentyl or hexyl, or branched, e.g. isopropyl, isobutyl, sec.-butyl, tert.-butyl, isopentyl, neopentyl or isohexyl.

Alkenyl—as a group per se and as a structural element of other groups and compounds, such as of halogenalkenyl—is either straight-chained, e.g. vinyl, 1-methylvinyl, allyl, 1-butenyl or 2-hexenyl, or branched, e.g. isopropenyl.

Alkinyl—as a group per se and as a structural element of other groups and compounds, such as of halogenalkinyl—is either straight-chained, e.g. propargyl, 2-butinyl or 5-hexinyl, or branched, e.g. 2-ethinylpropyl or 2-propargylisopropyl.

Alkylenedioxy is —O(alkylene)O—.

Alkylene is either straight-chained, e.g. —$CH_2CH_2$—, —$CH_2CH_2CH_2$— or —$CH_2CH_2CH_2CH_2$—, or branched, e.g. —CH($CH_3$)—, —CH($C_2H_5$)—, —C($CH_3$)$_2$—, —CH($CH_3$)$CH_2$— or —CH($CH_3$)CH($CH_3$)—.

Alkenylene is either straight-chained, e.g. vin-1,2-ylene, all-1,3-ylene, but-1-en-1,4-ylene or hex-2-en-1,6-ylene, or branched, e.g. 1-methylvin-1,2-ylene.

Alkinylene is either straight-chained, e.g. propargylene, 2-butinylene or 5-hexinylene, or branched, e.g. 2-ethinylpropylene or 2-propargylisopropylene.

Halogen is fluorine, chlorine, bromine or iodine, preferably fluorine, chlorine or bromine. Halogenalkyl may contain identical or different halogen atoms.

Aryl signifies phenyl or naphthyl, preferably phenyl.

Heteroaryl signifies a cyclic aromatic group with 5 to 9 ring members in one or two rings, of which 1 to 3 members are hetero atoms selected from the group oxygen, sulphur and nitrogen. 1 to 2 benzene rings may be condensed on the heterocycle, the binding to the residual molecule taking place either through the hetero or the benzene moiety.

Examples are benzimidazolyl, benzisoxazolyl, benzisothiazolyl, benzocumarinyl, benzofuryl, benzothiadiazolyl, benzothiazolyl, benzothienyl, benzoxazolyl, benzoxdiazolyl, quinazolinyl, quinolyl, quinoxalinyl, carbazolyl, dihydrobenzofuryl, furyl, imidazolyl, indazolyl, indolyl, isoquinolinyl, isothiazolyl, isoxazolyl, methylenedioxyphenyl, ethylenedioxyphenyl, naphthyridinyl, oxazolyl, phenanthridinyl, phthalazinyl, pteridinyl, pudnyl, pyrazinyl, pyrazolyl, pyridazinyl, pyrazolo[3,4-b]pyridyl, pyridyl, pyrimidinyl, pyrrolyl, tetrazolyl, oxadiazolyl, thiadiazolyl, thiazolyl, thienyl, triazinyl and triazolyl.

Preference is given to pyridyl, pyrazinyl, pyrimidinyl, thiazolyl, quinolinyl and thienyl.

Heterocyclyl signifies a 5- to 7-membered, non-aromatic ring with one to three hetero atoms selected from the group comprising N, O and S. Preference is given to non-aromatic 5- and 6-rings that have one nitrogen atom as a hetero atom and optionally one further hetero atom.

Preference is given to pyrazolinyl, thiazolinyl and oxazolinyl.

Of the compounds of formula I, those groups are preferred, wherein:

(1)
a) $R_1$ is methyl, ethyl or cyclopropyl, preferably methyl; or
b) $R_2$ is methyl, ethyl, fluoromethyl or trifluoroethyl, preferably methyl; or
c) $R_3$ is $C_1$–$C_6$-alkyl, $C_1$–$C_6$-alkoxy, $C_2$–$C_6$-alkenyl, $C_2$–$C_6$-alkenyloxy, $C_2$–$C_6$-alkinyl, $C_3$–$C_6$-alkinyloxy, $C_3$–$C_6$-cycloalkyl, $C_3$–$C_6$-cycloalkyloxy or $C_1$–$C_6$-alkoxycarbonyl, whereby the above-mentioned groups may be partially or wholly halogenated; furthermore CN, OCN or halogen; or
d) $R_3$ signifies phenyl which is unsubstituted or mono- to trisubstituted by identical or different substituents from halogen, $C_1$–$C_6$-alkyl, $C_1$–$C_6$-halogenalkyl, $C_1$–$C_6$-alkoxy, $C_1$–$C_6$-halogenalkoxy, $C_2$–$C_6$-alkenyl, $C_2$–$C_6$-alkenyloxy, $C_2$–$C_6$-alkinyl, $C_3$–$C_6$-alkinyloxy, $C_1$–$C_6$-alkoxycarbonyl, CN, OCN, optionally substituted benzyl, optionally substituted phenyl or optionally substituted phenoxy, whereby the above-mentioned aromatic groups may be substituted by one or more identical or different substituents selected from the group comprising halogen, cyano, nitro, $C_1$–$C_6$-alkyl, $C_1$–$C_6$-halogenalkyl, $C_1$–$C_6$-alkoxy, $C_1$–$C_6$halogenalkoxy, $C_1$–$C_6$-alkoxycarbonyl, $C_1$–$C_6$-alkythio, $C_1$–$C_6$-alkylamino, di-$C_1$–$C_6$-alkylamino and $C_2$–$C_6$-alkenyl; or
e) $R_3$ signifies phenyl which is substituted, preferably in 4-position, by $QR_4$, wherein Q is a direct bond, O, $OCH_2$, $CH_2O$, S, $CH_2$—$CH_2$, —CH=CH— or —C≡C— and $R_4$ signifies phenyl which is unsubstituted or mono- or disubstituted by identical or different substituents from halogen, $C_1$–$C_4$-alkyl, $C_1$–$C_4$-halogenalkyl, $C_1$–$C_4$-alkoxy, $C_1$–$C_4$-halogenalkoxy, $C_2$–$C_4$-alkenyl, $C_2$–$C_4$-alkenyloxy, $C_2$–$C_4$-alkinyl, $C_3$–$C_4$-alkinyloxy, $C_1$–$C_4$-alkoxycarbonyl or CN; or
f) $R_3$ signifies pyridyl, pyrimidinyl, furyl, thienyl, oxazolyl, isoxazolyl, thiazolyl, isothiazolyl, imidazolyl, pyrazolyl, which are unsubstituted or mono- to trisubstituted by identical or different substituents from halogen, cyano, nitro, aminocarbonyl, $C_1$–$C_4$-alkyl, $C_1$–$C_4$-halogenalkyl, $C_1$–$C_4$-alkylcarbonyl, $C_1$–$C_4$-alkylsulfonyl, $C_1$–$C_6$-alkylsulfoxyl, $C_3$–$C_6$-cycloalkyl, optionally substituted arylcarbonyl, $C_1$–$C_4$-alkoxy, $C_1$–$C_4$-halogenalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, di-$C_1$–$C_6$-alkylaminocarbonyl, or $C_2$–$C_6$-alkenyl; or
g) $R_5$ signifies hydrogen, or
h) $R_6$ and $R_7$ signify methyl or ethyl, preferably methyl.

(2) Compounds of formula I, wherein:
$R_1$ is methyl or ethyl, preferably methyl;
$R_2$ signifies methyl, ethyl, fluoromethyl or trifluoroethyl, preferably methyl;
$R_3$ signifies $C_1$–$C_6$-alkyl, $C_1$–$C_6$-alkoxy, $C_2$–$C_6$-alkenyl, $C_2$–$C_6$-alkenyloxy, $C_2$–$C_6$-alkinyl, $C_3$–$C_6$-alkinyloxy, $C_3$–$C_6$-cycloalkyl, $C_3$–$C_6$-cycloalkyloxy or $C_1$–$C_6$-alkoxycarbonyl, whereby the above-mentioned groups may be partly or wholly halogenated; furthermore CN, OCN or halogen; or
phenyl which is unsubstituted or mono- to trisubstituted by identical or different substituents from halogen, $C_1$–$C_6$-alkyl, $C_1$–$C_6$-halogenalkyl, $C_1$–$C_6$-alkoxy, $C_1$–$C_6$-halogenalkoxy, $C_2$–$C_6$-alkenyl, $C_2$–$C_6$-alkenyloxy, $C_2$–$C_6$-alkinyl, $C_3$–$C_6$-alkinyloxy, $C_1$–$C_6$-alkoxycarbonyl, CN, OCN, optionally substituted benzyl, optionally substituted phenyl or optionally substituted phenoxy, whereby the above-mentioned aromatic groups may be substituted by one or more identical or different substituents selected from the group comprising halogen, cyano, nitro, $C_1$–$C_6$-alkyl, $C_1$–$C_6$-halogenalkyl, $C_1$–$C_6$-alkoxy, $C_1$–$C_6$-halogenalkoxy, $C_1$–$C_6$-alkoxycarbonyl, $C_1$–$C_6$-alkylthio, $C_1$–$C_6$-alkylamino, di-$C_1$–$C_6$-alkylamino and $C_2$–$C_6$-alkenyl; or pyridyl, pyrimidinyl, furyl, thienyl, oxazolyl, isoxazolyl, thiazolyl, isothiazolyl, imidazolyl, pyrazolyl, which are unsubstituted or mono- to trisubstituted by identical or different substituents from halogen, cyano, nitro, aminocarbonyl, $C_1$–$C_4$-alkyl, $C_1$–$C_4$-halogenalkyl, $C_1$–$C_4$-alkylcarbonyl, $C_1$–$C_4$-alkylsulfonyl, $C_1$–$C_6$-alkylsulfoxyl, $C_3$–$C_6$-cycloalkyl, optionally substituted arylcarbonyl, $C_1$–$C_4$-alkoxy, $C_1$–$C_4$-halogenalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, or $C_2$–$C_6$-alkenyl; and
$R_6$ and $R_7$ signify methyl or ethyl, preferably methyl.

(2a) Of those mentioned under (2), especially those in which:
$R_3$ signifies phenyl which is unsubstituted or mono- to trisubstituted by identical or different substituents from halogen, $C_1$–$C_6$-alkyl, $C_1$–$C_6$-halogenalkyl, $C_1$–$C_6$-alkoxy, $C_1$–$C_6$-halogenalkoxy, $C_2$–$C_6$-alkenyl, $C_2$–$C_6$-alkenyloxy, $C_2$–$C_6$-alkinyl, $C_3$–$C_6$-alkinyloxy, $C_1$–$C_6$-alkoxycarbonyl, CN, OCN, optionally substituted benzyl, optionally substituted phenyl or optionally substituted phenoxy, whereby the above-mentioned aromatic groups may be substituted by one or more identical or different substituents selected from the group comprising halogen, cyano, nitro, $C_1$–$C_6$-alkyl, $C_1$–$C_6$-halogenalkyl, $C_1$–$C_6$-alkoxy, $C_1$–$C_6$-halogenalkoxy, $C_1$–$C_6$-alkoxycarbonyl, $C_1$–$C_6$-alkylthio, $C_1$–$C_6$-alkylamino, di-$C_1$–$C_6$-alkylamino and $C_2$–$C_6$-alkenyl.

(3) Compounds of formula I, wherein:
  $R_1$ is methyl or ethyl, preferably methyl;
  $R_2$ is $C_1$–$C_6$-alkyl or $C_1$–$C_6$-alkyl substituted by 1 to -5 fluorine atoms;
  $R_3$ is $C_1$–$C_6$alkyl, $C_1$–$C_6$-alkoxy, $C_1$–$C_6$-alkoxycarbonyl, CN, $C_3$–$C_6$-cycloalkyl, aryl, heteroaryl, heterocyclyl, aryloxy, heteroaryloxy or heterocyclyloxy, whereby, with the exception of CN, the above-mentioned groups may be substituted as mentioned above;
  $R_6$ and $R_7$ are methyl or ethyl, preferably methyl.

(3a) Of those mentioned under (3), especially those in which:
  $R_2$ is $C_1$–$C_6$-alkyl, fluoromethyl, difluoromethyl or 2,2,2-trifluoroethyl;
  $R_3$ is $C_1$–$C_6$-alkyl, $C_1$–$C_6$-alkoxy, $C_1$–$C_6$-alkoxycarbonyl, CN, $C_3$–$C_6$-cycloalkyl, phenyl which is unsubstituted or mono- to tni-substituted by identical or different substituents from halogen, $C_1$–$C_4$-alkyl, $C_1$–$C_4$-halogenalkyl, $C_1$–$C_4$-alkoxy, $C_1$–$C_4$-halogenalkoxy, $C_2$–$C_4$-alkenyl, $C_2$–$C_4$-alkenyloxy, $C_2$–$C_6$-alkinyl, $C_3$–$C_6$-alkinyloxy, CN, OCN, benzyl, phenyl, or phenyloxy, wherein these aromatic groups are unsubstituted or mono- or disubstituted by identical or different substituents from halogen, $C_1$–$C_2$-alkyl, $C_1$–$C_2$-halogenalkyl or $C_1$–$C_2$-alkoxy.

(3b) Of those mentioned under (3a), especially those in which:
  $R_3$ is $C_1$–$C_4$-alkyl, $C_1$–$C_4$-alkoxy, $C_1$–$C_6$-alkoxycarbonyl, or phenyl which is unsubstituted or mono- to disubstituted by halogen, $C_1$–$C_2$-alkyl, $C_1$–$C_2$-halogenalkyl or $C_1$–$C_2$-alkoxy.

(4) Compounds of formula I, wherein:
  $R_1$ is methyl, ethyl or cyclopropyl, preferably methyl;
  $R_2$ is $C_1$–$C_6$-alkyl, preferably methyl or ethyl;
  $R_3$ is $C_1$–$C_6$-alkyl, $C_1$–$C_6$-halogenalkyl, $C_2$–$C_6$-alkenyl, $C_1$–$C_6$-alkoxy, $C_2$–$C_6$-alkenyloxy, $C_1$–$C_6$-alkoxycarbonyl, CN, $C_3$–$C_6$-cycloalkyl, aryl, heteroaryl, heterocyclyl, aryloxy, heteroaryloxy or heterocyclyloxy, whereby the hydrocarbon radicals and the cyclic radicals may be substituted as mentioned above;

(4a) Of those mentioned under (4), especially those in which:
  $R_3$ is $C_1$–$C_6$-alkyl, $C_1$–$C_6$-halogenalkyl, $C_2$–$C_6$-alkenyl, $C_1$–$C_6$-alkoxy, $C_2$–$C_6$-alkenyloxy, $C_1$–$C_6$-alkoxycarbonyl, $C_3$–$C_6$-cycloalkyl.

(4b) Of those mentioned under (4), especially those in which:
  $R_3$ is phenyl which is unsubstituted or mono- or disubstituted by halogen, $C_1$–$C_4$-alkyl, $C_1$–$C_4$-halogenalkyl, $C_1$–$C_4$-alkoxy, $C_1$–$C_4$-halogenalkoxy, $C_2$–$C_4$-alkenyl, $C_2$–$C_4$-alkenyloxy, benzyl, phenyl, or phenyloxy, wherein these aromatic groups are unsubstituted or mono- or disubstituted by halogen, $C_1$–$C_2$-alkyl, $C_1$–$C_2$-halogenalkyl or $C_1$–$C_2$-alkoxy.

(5) Compounds of formula I, wherein:
  $R_1$ signifies methyl, ethyl or cyclopropyl;
  $R_2$ signifies $C_1$–$C_6$-alkyl, preferably methyl or ethyl, $C_2$–$C_6$-alkenyl, preferably allyl or $C_2$–$C_6$-alkinyl, preferably propargyl.
  $R_3$ signifies phenyl which may be substituted by one or more identical or different substituents selected from the group comprising halogen, $C_1$–$C_6$-alkyl, $C_1$–$C_6$-alkoxy, halogen-$C_1$–$C_6$-alkoxy, halogen-$C_1$–$C_6$-alkyl, $C_1$–$C_6$-alkylthio, halogen-$C_1$–$C_6$-alkylthio, $C_1$–$C_6$-alkylsulfinyl, halogen-$C_1$–$C_6$-alkylsulfinyl, $C_1$–$C_6$-alkyl-sulfonyl, halogen-$C_1$–$C_6$-alkylsulfonyl, $C_2$–$C_6$-alkenyl, $C_2$–$C_6$-alkenyloxy, $C_2$–$C_6$-alkinyl, $C_3$–$C_6$-alkinyloxy, $C_1$–$C_6$-alkylcarbonyl, halogen-$C_1$–$C_6$-alkylcarbonyl, $C_1$–$C_6$-alkoxycarbonyl, halogen-$C_1$–$C_6$-alkoxycarbonyl, $C_1$–$C_6$-alkylaminocarbonyl, di-($C_1$–$C_6$-alkyl)-aminocarbonyl, whereby the alkyl groups may be identical or different, $C_1$–$C_6$-alkylaminothiocarbonyl, di-($C_1$–$C_6$-alkyl)-aminothiocarbonyl, whereby the alkyl groups may be identical or different, $C_1$–$C_6$-alkylamino, di-($C_1$–$C_6$-alkyl)-amino, $NO_2$, an unsubstituted $C_1$–$C_4$-alkylenedioxy group or one which is mono- to tetra-substituted by $C_1$–$C_4$-alkyl and/or by halogen; or CN, $SF_5$, OH and $QR_4$;

Q signifies a direct bond, O, O($C_1$–$C_6$-alkylene), ($C_1$–$C_6$-alkylene)O, $C_1$–$C_8$-alkylene, $C_2$–$C_6$-alkenylene or $C_2$–$C_6$-alkinylene;

$R_4$ signifies an unsubstituted or mono- to penta-substituted $C_3$–$C_6$-cycloalkyl, aryl, heteroaryl or heterocyclyl group, whereby the substituents are selected from the group comprising halogen, $C_1$–$C_6$-alkyl, halogen-$C_1$–$C_6$-alkyl, $C_1$–$C_6$-alkoxy, halogen-$C_1$–$C_6$-alkoxy, phenoxy, CN, $SF_5$, $NO_2$, $C_1$–$C_6$-alkylsulfinyl, halogen-$C_1$–$C_6$-alkylsulfinyl, $C_1$–$C_6$-alkylsulfonyl, halogen-$C_1$–$C_6$-alkylsulfonyl and an unsubstituted $C_1$–$C_4$-alkylenedioxy or one that is mono- to tetra-substituted by $C_1$–$C_4$-alkyl and/or by halogen.

(5a) Of those mentioned under (5), especially those in which:
  $R_3$ signifies phenyl which is substituted, preferably in 4-position, by $QR_4$, wherein Q is a direct bond, O, $OCH_2$, $CH_2O$, S, $CH_2$—$CH_2$, —CH=CH— or —C≡C— and
  $R_4$ signifies phenyl which is unsubstituted or mono- or disubstituted by identical or different substituents from halogen, $C_1$–$C_4$-alkyl, $C_1$–$C_4$-halogenalkyl, $C_1$–$C_4$-alkoxy, $C_1$–$C_4$-halogenalkoxy, $C_2$–$C_4$-alkenyl, $C_2$–$C_4$-alkenyloxy, $C_2$–$C_4$-alkinyl, $C_3$–$C_4$-alkinyloxy, $C_1$–$C_4$-alkoxycarbonyl or CN.

Compounds of formula I may be produced as follows:

A) A compound of formula I is produced whereby a hydrazone of the general formula II

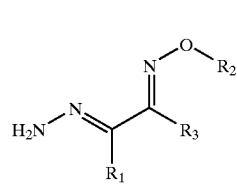

II wherein $R_1$, $R_2$ and $R_3$ have the significances given for formula I, is reacted with an aldehyde or a ketone of the general formula III or with one of its acetal or imino derivatives of the general formulae IVa and IVb

III

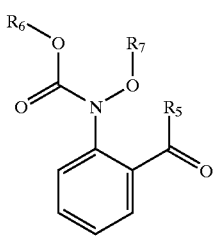

IVa

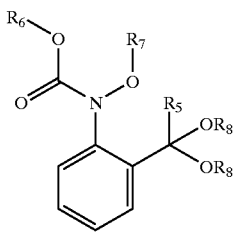

IVb

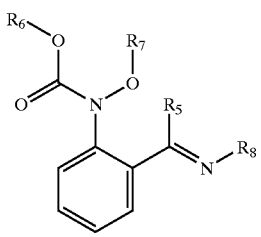

wherein $R_8$ signifies optionally substituted $C_1$–$C_6$-alkyl or the two $R_8$, together with the two oxygen atoms and the carbon to which they are bonded, signify a cyclic acetal.

The compounds of the general formulae II and III are known from literature (e.g. Ablov et al., Russ.J.Inorg.Chem. (Engl.Transl.), 11, 1966, 39,40; Barton, Derek H. R.; Bashiardes, George; Fourrey, Jan-Louis, Tetrahedron, 44, 1, 1988, 147–162; WO 93/15046) or may be produced by methods known per se. The compounds of the general formulae IVa and IVb may be obtained analogously to the methods described under B) and C) or directly from the carbonyl derivatives of formula III.

B) A compound of formula I is produced whereby a N-hydroxycarbamate of the general formula V,

V

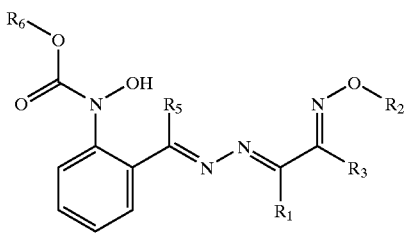

wherein $R_1$—$R_3$, $R_5$ and $R_6$ are defined as for formula I, is etherified. The compounds of the general formula V are novel and may be produced whereby a) a N-hydroxyaniline of the general formula VI

VI

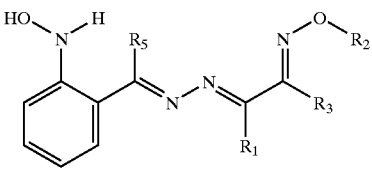

wherein $R_1$—$R_3$ and $R_5$ have the significances given for formula I, is reacted with a chloroformic acid ester of the general formula VII $$Cl\text{—}COOR_6 \qquad \text{VII}$$

or b) a carbonyl compound of the general formula VIII

VIII

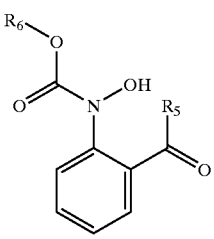

VIIIa

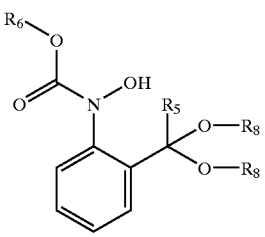

VIIIb

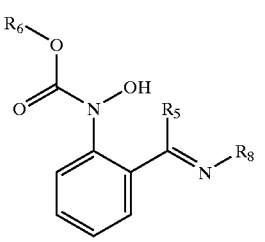

wherein $R_5$ and $R_6$ have the significances given for formula I, or one of its acetal or imino derivatives VIIIa or VIIIb, is condensed with a hydrazone of the general formula II.

The compounds of formula VI are novel and may be produced by one of the following methods:

aa) a hydrazone of the general formula II is condensed with an aldehyde or ketone of the general formula IX or with one of its acetal or imino derivatives IXa or IXb

IX

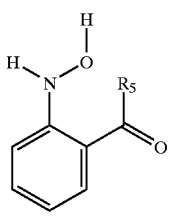

IXa

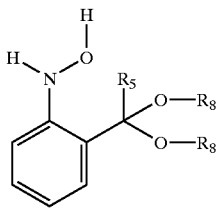

IXb

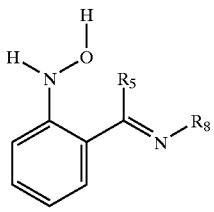

wherein $R_5$ is defined as for formula I and $R_8$ is defined as for formula IV. The compounds of formula IX are known (e.g. Bamberger, Elger; Chem. Ber. 36, 3653 (1903); Fijalek, Z.; Zuman, P.; Electroanalysis 5, 53 (1993); Barth, A.; et al.; J.Am. Chem Soc. 119, 4149 (1997); Karakus C.; Zuman, P.; J.Electronanal. Chem. 396, 499 (1995)) and the acetal and imino derivatives thereof may be produced by methods known per se.

ab) a hydrazone of the general formula X

X

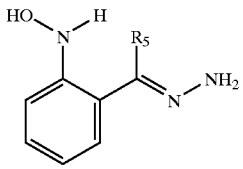

wherein $R_5$ signifies hydrogen or methyl, is condensed with a ketone of formula XI

XI

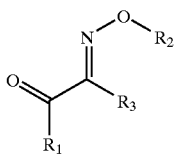

wherein $R_1$ to $R_3$ are as defined under formula I.

The compounds of formulae X and XI are known (e.g. Buhlmann; Einhorn; Chem. Ber. 34, 3791 (1901)) or may be produced by methods known per se.

ac) A nitro compound of the general formula XII

XII

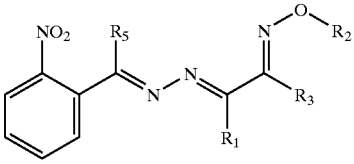

wherein $R_1$—$R_3$ and $R_5$ are as defined under formula I, is reduced analogously to the methods indicated for the preparation of compounds of formula IX. The compounds of formula XII are novel and may be obtained e.g. by condensation of the corresponding nitrocarbonyl derivatives with hydrazones of formula II.

The compounds of formula VIII are novel and may be prepared by reacting a hydroxyaniline of formula IX with a chloroformic acid ester of formula VII.

C) A compound of formula I is produced whereby an alkoxyaniline of the general formula XIII

XIII

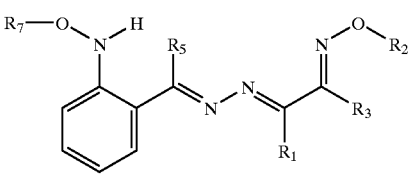

wherein $R_1$—$R_3$, $R_5$ and $R_7$ are defined as for formula I, is reacted with a chloroformic acid ester of the general formula VII.

The compounds of formula XIII are novel and may be produced by one of the following methods:

a) A hydrazone of formula II is condensed with an aldehyde or ketone of the general formula XIV or with one of its acetal or imino derivatives

XIV

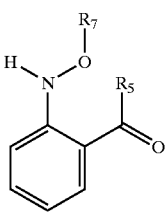

XVa

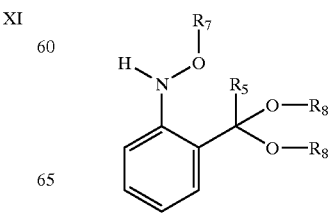

-continued

XVb

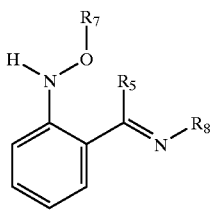

wherein R₅ and R₇ are defined as for formula I and R₈ is defined as for formula IV.

The compounds of formulae XIV, XVa and XVb are novel and may be prepared by etherification of the N-hydroxy derivatives of formula IX.

b) A ketone of formula XI is condensed with a hydrazone of the general formula XVI

XVI

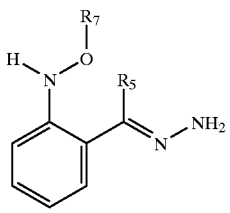

wherein R₅ and R₇ are as defined under formula I.

The compounds of formulae XVI are novel and may be prepared by etherificafion of the N-hydroxy derivatives of formula X.

D) A compound of formula I is produced whereby an oxime of the general formula XVII

XVII

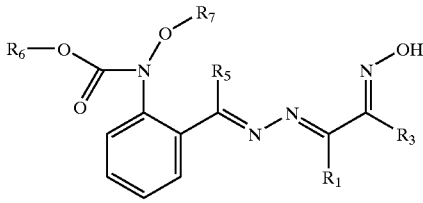

wherein R₁, R₃, and R₅ to R₇ are defined as for formula I, is etherified.

The compounds of formula XVII are novel and may be obtained whereby a) a ketone of the general formula XVIII

XVIII

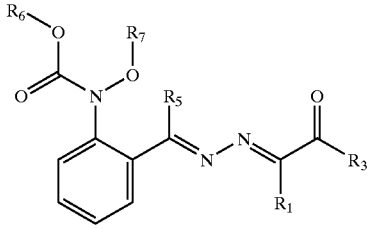

wherein R₁, R₃ and R₅—R₇ have the significances given for formula I, is reacted with hydroxylamine or with one of its salts, or b) a compound of the general formula XIX,

XIX

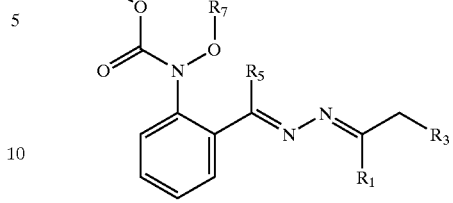

wherein R₁, R₃ and R₅—R₇ are defined as for formula I, is reacted with nitrous acid or with an alkyl nitrite in the presence of an acid or base, or c) a hydrazone of the general formula XX

XX

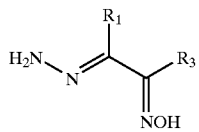

wherein R₁ and R₃ are defined as for formula I, is reacted with an aldehyde or ketone of the general formula III or with an acetal or imine of the general formulae IVa or IVb, as a described under A).

The compounds of formulae XVIII and XIX are novel and may be obtained analogously to the preparation of the compounds of formula I.

The compounds of formula XX are known (e.g. Barany et al., J.Chem.Soc., 1951, 1929; Neber; Hartung; Ruopp, Chem.Ber., 58, 1925, 1240; Gnichtel, Horst; Toepper, Bernhard, Liebigs Ann.Chem., GE, 1989, 1071–1074; Rapoport,H.; Nilsson,W., J.Amer.Chem.Soc., 83, 1961, 4262–4267).

E) A compound of formula I may be produced whereby a ketone of the general formula XVIII is reacted with an alkoxyamine of the general formula XXI

R₂—ONH₂    XXI wherein R₂ is defined as for formula I, or with one of its salts.

All the above-described reactions are known per se. The novel, above-mentioned intermediates were developed especially for the present invention and similarly form an object of this invention. Those of formulae IV, V, VI, VIII, XII–XIX are of particular significance.

The compounds of formula I are of preventive and/or curative merit as active ingredients for the control of plant pests and may be used in the agricultural sector and related fields The active ingredients of formula I according to the invention are notable for their good activity even at low concentrations, for their good plant tolerance and for their environmental acceptability. They possess very advantageous, especially systemic properties, and may be used for the protection of numerous cultivated plants. Using the active ingredients of formula I, pests appearing on plants or plant parts (fruits, flowers, foliage, stems, tubers, roots) of different crops can be checked or destroyed, whereby parts of the plant which grow later are also protected e.g. from phytopathogenic micro-organisms.

The compounds of formula I may also be be employed as a dressing for seeds (fruits, tubers, grain) and plant cuttings to protect against fungal infections, and to protect against phytopathogenic fungi appearing in the soil.

Compounds I are effective for example against the phytopathogenic fungi belonging to the following classes: Fungi imperfecti (e.g. Botrytis, Pyricularia, Helminthosporium, Fusarium, Septoria, Cercospora and Alternaria); Basidiomycetes (e.g. Rhizoctonia, Hemileia, Puccinia); Ascomycetes (e.g. Venturia and Erysiphe, Podosphaera, Monilinia, Uncinula) and Oomycetes (e.g. Phytophthora, Pythium, Plasmopara).

Target cultivations for the plant-protecting usage in the context of the invention are, for example, the following species of plant: cereals, (wheat, barley, rye, oats, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybean); oleaginous fruits (rape, mustard, poppy, olives, sunflowers, coconut, castor oil plants, cocoa beans, groundnuts); cucumber plants (squashes, cucumbers, melons); fibrous plants (cotton, flax, hemp or jute); citrus fruits (oranges, lemons, grapefruit, mandarins); vegetables (spinach, lettuce, asparagus, cabbages, carrots, onions, tomatoes, potatoes, paprika); Lauraceae (avocado, cinnamon, camphor); and plants such as tobacco, nuts, coffee, aubergines, sugar cane, tea, pepper, vines, hops, banana plants, natural rubber plants and ornamental.

In addition, the compounds of formula I according to the invention are valuable active ingredients against insects and pests of the order Acarina, such as those appearing on crop plants and ornamentals in agriculture and horticulture and in forestry, whilst being tolerated well by warm-blooded animals, fish and plants. The compounds of formula I are especially suitable for controlling pests in cultivations of cotton, vegetables, fruit and rice, such as spider mites, aphids, caterpillars and plant and leaf hoppers in rice. The pests which are primarily controlled are spider mites such as *Panonychus ulmi,* aphids such as *Aphis craccivora,* caterpillars such as those of *Heliothis virescens* and plant and leaf hoppers in rice, such as *Nilaparvata lugens* or *Nephotettix cincticeps.*

The good pesticidal activity of the compounds I according to the invention corresponds to a mortality rate of at least 50–60% of the pests mentioned.

Further fields of application for the active ingredients according to the invention are the protection of stock and material, where the goods stored are protected against rotting and mildew, as well as against animal pests (e.g. grain weevils, mites, maggots, etc). In the hygiene sector, compounds of formula I provide successful control of animal parasites such as ticks, mites, warble flies etc., on domestic animals and productive livestock Compounds I are effective against individual or all stages of development of pests showing normal sensitivity, and also of those showing resistance Their activity may be demonstrated, for example, by the mortality of the pests, which occurs immediately or only after some time, for example during a moult, or by reduced egg laying and/or hatching rate.

Compounds I are used in this instance in unmodified form or preferably together with the excipients that are usual in formulation technology. To this end, they are suitably processed in known manner e.g. into emulsifiable concentrates, coatable pastes, directly sprayable or dilutable solutions, diluted emulsions, wettable powders, soluble powders, dusts or granules, e.g. by encapsulation in e.g. polymeric substances. As with the type of compositions, the methods of application, such as spraying, atomising, dusting, scattering, coating or pouring, are selected in accordance with the intended objectives and the prevailing circumstances.

Suitable carriers and additives may be solid or liquid and are substances that are appropriate in formulation technology, for example natural or regenerated mineral substances, solvents, dispersants, wetting agents, tackifiers, thickeners, binding agents or fertilisers.

The compounds of formula I may be mixed with further active ingredients, e.g. fertilisers, trace element intermediates or other plant-protecting compositions, especially with further fungicides. Unexpected synergistic effects may thus occur.

Preferred mixture components are:

azoles, such as azaconazole, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, tebuconazole, tetraconazole, triadimefon, triadimenol, triflumizole, tritconazole; pynmidinyl carbinols, such as ancymidol, fenarimol, nuarimol; 2-amino-pyrimidines, such as bupinmate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozolin; carboxamides, such as carboxin, fenfuram, flutolanil, mepronil, oxycarboxin, thifluzamide; guanidines, such as guazatine, dodine, iminoctadine;

strobilurines, such as azoxystrobin, kresoxim-methyl, metominostrobin, SSF-129, CGA 279202 (trifloxystrobin); dithiocarbamates, such as ferbam, mancozeb, maneb, metiram, propineb, thiram, zineb, ziram; N-halogenmethylthiophthalimides, such as captafol, captan, dichlofluanid, fluoromide, folpet, tolyfluanid; Cu compounds, such as Bordeaux mixture, copper hydroxide, copper oxychloride, copper sulfate, cuprous oxide, mancopper, oxine-copper; nitrophenol derivatives, such as dinocap, nitrothal-isopropyl; organo-P derivatives, such as edifenphos, iprobenphos, isoprothiolane, phosdiphen,. pyrazophos, tolclofos-methyl; various, such as AC 382042, acibenzolar-S-methyl, anilazine, blasticidin-S, quinomethionat, chloroneb, chlorothalonil, cymoxanil, dichlone, diclomezine, dicloran, diethofencarb, dimethomorph, dithianon, etridiazole, famoxadone, fenamidone, fenhexamid, fentin, ferimzone, fluazinam, flusulfamide, fosetyl-aluminium, hymexazol, IKF-916, iprovalicarb, kasugamycin, methasulfocarb, MON65500, pencycuron, phthalide, polyoxins, probenazole, propamocarb, pyroquilon, quinoxyfen, quintozene, RH-7281, RPA 407213, sulfur, triazoxide, tricyclazole, triforine, validamycin.

One preferred method of applying an active ingredient of formula I or an agrochemical composition containing at least one of these active ingredients is application to the foliage (leaf application). The frequency and rate of application depend on the severity of infestation by the invader in question. However, the active ingredients I can also penetrate the plant through the roots via the soil (systemic action) by drenching the locus of the plants with a liquid preparation, or by applying the substances to the soil in solid form, for example in granular form (soil application). With paddy rice cultures, granules may be metered into the flooded paddy field. The compounds I may also be applied to seed grain for seed pre-treatment (coating) by either drenching the grains or tubers in a liquid preparation of the active ingredient or coating them with a solid preparation. The compositions are prepared in known manner, e.g. by intimately mixing and/or grinding the active ingredient with extenders, such as solvents, solid carriers and optionally surface-active compounds (surfactants).

The agrochemical compositions normally contain 0.1 to 99 percent by weight, especially 0.1 to 95 percent by weight, of active ingredient of formula 1, 99.9 to 1 percent by weight, especially 99.8 to 5 percent by weight, of a solid or liquid additive and 0 to 25 percent by weight, especially 0.1 to 25 percent by weight, of a surfactant.

Favourable application rates generally lie between 1 g and 2 kg of active substance (AS) per hectare (ha), preferably between 10 g and 1 kg AS/ha, especially between 20 g and 600 g AS/ha.

For usage as a seed dressing, the dosages advantageously used are 10 mg to 1 g of active substance per kg seeds.

Whereas it is preferred to formulate commercial products as concentrates, the end user will normally use dilute formulations.

The compositions may also contain further additives, such as stabilisers, anti4oaming agents, viscosity regulators, binding agents or tackifiers, as well as fertilisers or other active ingredients, in order to achieve special effects.

Preparation Example

P-1) N-(2-formylphenyl)N-methoxycarbamic acid methyl ester

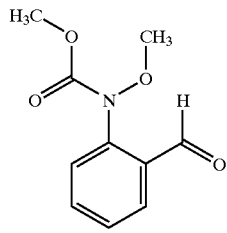

A solution of 27.4 g of (2-bromomethyl-phenyl)-N-methoxycarbamic acid methyl ester in 50 ml of acetonitrile is added dropwise at room temperature to 40 g of N-methyl-morpholine-N-oxide in 150 ml of acetonitrile. After stirring for 16 hours, the mixture is concentrated and the residue partitioned between ethyl acetate and water. The aqueous phase is extracted with ethyl acetate and, after drying over sodium sulphate, the solvent is distilled from the combined organic phases. The residue is purified on silica gel using ethyl acetate/hexane (1:5% by volume). The title compound is obtained in the form of a yellow oil.

H-2) N-methoxy-{2-[(2-methoxyimino-1-methyl-2-(4-fluorophenyl)-ethylidene)-hydrazonomethyl]-phenyl}-carbamic acid methyl ester

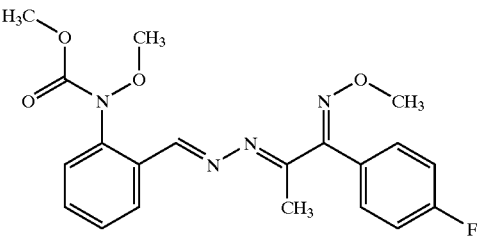

A solution of 1.05 g of (2-formyl-phenyl)-N-methoxycarbamic acid methyl ester and 1.05 g of 1-(4-fluorophenyl)-2-hydrazono-propan-1-on-O-methyl-oxime in 5 ml of methanol is stirred at room temperature for 4 hours. The resulting by-product (symmetric azine of 1-(4-fluorophenyl)-2-hydrazono-propan-1-on-O-methyl-oxime) is removed by filtration and the filtrate is placed in a refrigerator over night. The product which has crystallised is filtered off (1.0 g). By concentrating the mother liquor and by means of fractional crystallisation of the residue, a further 0.48 g of the title compound are obtained in the form of yellow crystals having a melting point of 88–90° C.

The compounds of the following tables may be produced in analogous manner. Abbreviations: i: iso; s: sec; t: tert
Table 1
Compounds of the general formula I.1, in which $R_2$, $R_6$ and $R_7$ signify methyl and $R_3$ corresponds in each case to one line of Table A.

I.1

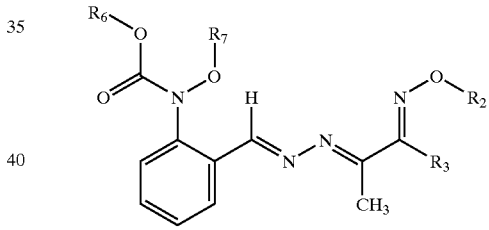

Table 2
Compounds of the general formula I.1, in which $R_2$ signifies ethyl and $R_6$ and $R_7$ signify methyl and $R_3$ corresponds in each case to one line of Table A.
Table 3
Compounds of the general formula I.1, in which $R_2$ signifies difluoromethyl and $R_6$ and $R_7$ signify methyl and $R_3$ corresponds in each case to one line of Table A.
Table 4
Compounds of the general formula I.1, in which $R_2$ signifies 2,2,2-trifluoroethyl and $R_6$ and $R_7$ signify methyl and $R_3$ corresponds in each case to one line of Table A.
Table 5
Compounds of the general formula I.1, in which $R_2$ and $R_6$ signify methyl and $R_7$ signifies ethyl and $R_3$ corresponds in each case to one line of Table A.
Table 6
Compounds of the general formula I.1, in which $R_2$ and $R_7$ signify ethyl and $R_6$ signifies methyl and $R_3$ corresponds in each case to one line of Table A.
Table 7
Compounds of the general formula I.1, in which $R_2$ and $R_6$ signify ethyl and $R_7$ signifies methyl and $R_3$ corresponds in each case to one line of Table A.

Table 8
Compounds of the general formula I.1, in which $R_2$ signifies methyl and $R_6$ and $R_7$ signify ethyl and $R_3$ corresponds in each case to one line of Table A.

Table 9
Compounds of the general formula I.1, in which $R_2$, $R_6$ and $R_7$ signify ethyl and $R_3$ corresponds in each case to one line of Table A.

Table 10
Compounds of the general formula I.1, in which $R_2$ signifies n-propyl and $R_6$ and $R_7$ signify methyl and $R_3$ corresponds in each case to one line of Table A.

Table 11
Compounds of the general formula I.2, in which $R_2$, $R_6$ and $R_7$ signify methyl and $R_3$ corresponds in each case to one line of Table A.

I.2

Table 12
Compounds of the general formula I.2, in which $R_2$ signifies ethyl and $R_6$ and $R_7$ signify methyl and $R_3$ corresponds in each case to one line of Table A.

Table 13
Compounds of the general formula I.2, in which $R_2$ signifies difluoromethyl and $R_6$ and $R_7$ signify methyl and $R_3$ corresponds in each case to one line of Table A.

Table 14
Compounds of the general formula I.2, in which $R_2$ signifies 2,2,2-trifluoroethyl and $R_8$ and $R_7$ signify methyl and $R_3$ corresponds in each case to one line of Table A.

Table 15
Compounds of the general formula I.2, in which $R_2$ and $R_6$ signify methyl and $R_7$ signifies ethyl and $R_3$ corresponds in each case to one line of Table A.

Table 16
Compounds of the general formula I.2, in which $R_2$ and $R_7$ signify ethyl and $R_6$ signifies methyl and $R_3$ corresponds in each case to one line of Table A.

Table 17
Compounds of the general formula I.2, in which $R_2$ and $R_6$ signify ethyl and $R_7$ signifies methyl and $R_3$ corresponds in each case to one line of Table A.

Table 18
Compounds of the general formula I.2, in which $R_2$ signifies methyl and $R_6$ and $R_7$ signify ethyl and $R_3$ corresponds in each case to one line of Table A.

Table 19
Compounds of the general formula I.2, in which $R_2$, $R_6$ and $R_7$ signify ethyl and $R_3$ corresponds in each case to one line of Table A.

Table 20
Compounds of the general formula I.2, in which $R_2$ signifies n-propyl and $R_6$ and $R_7$ signify methyl and $R_3$ corresponds in each case to one line of Table A.

Table 21
Compounds of the general formula I.3, in which $R_2$, $R_6$ and $R_7$ signify methyl and $R_3$ corresponds in each case to one line of Table A.

I.3

Table 22
Compounds of the general formula I.3, in which $R_2$ signifies ethyl and $R_6$ and $R_7$ signify methyl and $R_3$ corresponds in each case to one line of Table A.

Table 23
Compounds of the general formula I.3, in which $R_2$ signifies difluoromethyl and $R_6$ and $R_7$ signify methyl and $R_3$ corresponds in each case to one line of Table A.

Table 24
Compounds of the general formula I.3, in which $R_2$ signifies 2,2,2-trifluoroethyl and $R_6$ and $R_7$ signify methyl and $R_3$ corresponds in each case to one line of Table A.

Table 25
Compounds of the general formula I.3, in which $R_2$ and $R_6$ signify methyl and $R_7$ signifies ethyl and $R_3$ corresponds in each case to one line of Table A.

Table 26
Compounds of the general formula I.3, in which $R_2$ and $R_7$ signify ethyl and $R_6$ signifies methyl and $R_3$ corresponds in each case to one line of Table A.

Table 27
Compounds of the general formula I.3, in which $R_2$ and $R_6$ signify ethyl and $R_7$ signifies methyl and $R_3$ corresponds in each case to one line of Table A.

Table 28
Compounds of the general formula I.3, in which $R_2$ signifies methyl and $R_6$ and $R_7$ signify ethyl and $R_3$ corresponds in each case to one line of Table A.

Table 29
Compounds of the general formula I.3, in which $R_2$, $R_6$ and $R_7$ signify ethyl and $R_3$ corresponds in each case to one line of Table A.

Table 30
Compounds of the general formula I.3, in which $R_2$ signifies n-propyl and $R_6$ and $R_7$ signify methyl and $R_3$ corresponds in each case to one line of Table A.

Table 31
Compounds of the general formula I.4, in which $R_2$, $R_6$ and $R_7$ signify methyl and $R_3$ corresponds in each case to one line of Table A.

I.4

Table 32
Compounds of the general formula I.4, in which $R_2$ signifies ethyl and $R_6$ and $R_7$ signify methyl and $R_3$ corresponds in each case to one line of Table A.

Table 33
Compounds of the general formula I.4, in which $R_2$ signifies difluoromethyl and $R_6$ and $R_7$ signify methyl and $R_3$ corresponds in each case to one line of Table A.

Table 34
Compounds of the general formula I.4, in which $R_2$ signifies 2,2,2-trifluoroethyl and $R_6$ and $R_7$ signify methyl and $R_3$ corresponds in each case to one line of Table A.

Table 35
Compounds of the general formula I.4, in which $R_2$ and $R_6$ signify methyl and $R_7$ signifies ethyl and $R_3$ corresponds in each case to one line of Table A.

Table 36
Compounds of the general formula I.4, in which $R_2$ and $R_7$ signify ethyl and $R_6$ signifies methyl and $R_3$ corresponds in each case to one line of Table A.

Table 37
Compounds of the general formula I.4, in which $R_2$ and $R_6$ signify ethyl and $R_7$ signifies methyl and $R_3$ corresponds in each case to one line of Table A.

Table 38
Compounds of the general formula I.4, in which $R_2$ signifies methyl and $R_6$ and $R_7$ signify ethyl and $R_3$ corresponds in each case to one line of Table A.

Table 39
Compounds of the general formula I.4, in which $R_2$, $R_6$ and $R_7$ signify ethyl and $R_3$ corresponds in each case to one line of Table A.

Table 40
Compounds of the general formula I.4, in which $R_2$ signifies n-propyl and $R_6$ and $R_7$ signify methyl and $R_3$ corresponds in each case to one line of Table A.

Table 41
Compounds of the general formula I.5, in which $R_2$, $R_6$ and $R_7$ signify methyl and $R_3$ corresponds in each case to one line of Table A.

I.5

Table 42
Compounds of the general formula I.5, in which $R_2$ signifies ethyl and $R_6$ and $R_7$ signify methyl and $R_3$ corresponds in each case to one line of Table A.

Table 43
Compounds of the general formula I.5, in which $R_2$ signifies difluoromethyl and $R_6$ and $R_7$ signify methyl and $R_3$ corresponds in each case to one line of Table A.

Table 44
Compounds of the general formula I.5, in which $R_2$ signifies 2,2,2-trifluoroethyl and $R_6$ and $R_7$ signify methyl and $R_3$ corresponds in each case to one line of Table A.

Table 45
Compounds of the general formula I.5, in which $R_2$ and $R_6$ signify methyl and $R_7$ signifies ethyl and $R_3$ corresponds in each case to one line of Table A.

Table 46
Compounds of the general formula I.5, in which $R_2$ and $R_7$ signify ethyl and $R_6$ signifies methyl and $R_3$ corresponds in each case to one line of Table A.

Table 47
Compounds of the general formula I.5, in which $R_2$ and $R_6$ signify ethyl and $R_7$ signifies methyl and $R_3$ corresponds in each case to one line of Table A.

Table 48
Compounds of the general formula I.5, in which $R_2$ signifies methyl and $R_6$ and $R_7$ signify ethyl and $R_3$ corresponds in each case to one line of Table A.

Table 49
Compounds of the general formula I.5, in which $R_2$, $R_6$ and $R_7$ signify ethyl and $R_3$ corresponds in each case to one line of Table A.

Table 50
Compounds of the general formula I.5, in which $R_2$ signifies n-propyl and $R_6$ and $R_7$ signify methyl and $R_3$ corresponds in each case to one line of Table A.

Table 51
Compounds of the general formula I.6, in which $R_2$, $R_6$ and $R_7$ signify methyl and $R_3$ corresponds in each case to one line of Table A.

I.6

Table 52
Compounds of the general formula I.6, in which $R_2$ signifies ethyl and $R_6$ and $R_7$ signify methyl and $R_3$ corresponds in each case to one line of Table A.

Table 53
Compounds of the general formula I.6, in which $R_2$ signifies difluoromethyl and $R_6$ and $R_7$ signify methyl and $R_3$ corresponds in each case to one line of Table A.

Table 54
Compounds of the general formula I.6, in which $R_2$ signifies 2,2,2-trifluoroethyl and $R_6$ and $R_7$ signify methyl and $R_3$ corresponds in each case to one line of Table A.

Table 55
Compounds of the general formula I.6, in which $R_2$ and $R_6$ signify methyl and $R_7$ signifies ethyl and $R_3$ corresponds in each case to one line of Table A.

Table 56
Compounds of the general formula I.6, in which $R_2$ and $R_7$ signify ethyl and $R_6$ signifies methyl and $R_3$ corresponds in each case to one line of Table A.

Table 57
Compounds of the general formula I.6, in which $R_2$ and $R_6$ signify ethyl and $R_7$ signifies methyl and $R_3$ corresponds in each case to one line of Table A.

Table 58
Compounds of the general formula I.6, in which $R_2$ signifies methyl and $R_6$ and $R_7$ signify ethyl and $R_3$ corresponds in each case to one line of Table A.

Table 59
Compounds of the general formula I.6, in which $R_2$, $R_6$ and $R_7$ signify ethyl and $R_3$ corresponds in each case to one line of Table A.

Table 60
Compounds of the general formula I.6, in which $R_2$ signifies n-propyl and $R_6$ and $R_7$ signify methyl and $R_3$ corresponds in each case to one line of Table A.

TABLE A

| No. | R₃ |
|---|---|
| 1. | CH₃ |
| 2. | CH₂CH₃ |
| 3. | (CH₂)₂CH₃ |
| 4. | (CH₂)₃CH₃ |
| 5. | (CH₂)₄CH₃ |
| 6. | (CH₂)₅CH₃ |
| 7. | CH(CH₃)₂ |
| 8. | C(CH₃)₃ |
| 9. | CH₂CH(CH₃)₂ |
| 10. | CH(CH₃)CH₂CH₃ |
| 11. | OCH₃ |
| 12. | OCH₂CH₃ |
| 13. | O(CH₂)₂CH₃ |
| 14. | O(CH₂)₃CH₃ |
| 15. | O(CH₂)₄CH₃ |
| 16. | OCH(CH₃)₂ |
| 17. | OCH(CH₃)CH₂CH₃ |
| 18. | OC(CH₃)₃ |
| 19. | CH=CH₂ |
| 20. | CH=CHCH₃ |
| 21. | CH=C(CH₃)₂ |
| 22. | CH₂CH=CH₂ |
| 23. | CH₂CH=CHCH₃ |
| 24. | OCH₂CH=CH₂ |
| 25. | C≡CH |
| 26. | C≡CCH₃ |
| 27. | C≡CC(CH₃)₃ |
| 28. | CH₂C≡CH |
| 29. | CH₂C≡CCH₃ |
| 30. | OCH₂C≡CH₃ |
| 31. | OCH₂C≡C—C(CH₃)₃ |
| 32. | C(O)OCH₃ |
| 33. | C(O)OCH₂CH₃ |
| 34. | C(O)O(CH₂)₂CH₃ |
| 35. | C(O)O(CH₂)₃CH₃ |
| 36. | C(O)O(CH₂)₄CH₃ |
| 37. | C(O)OCH(CH₃)₂ |
| 38. | C(O)OC(CH₃)₃ |
| 39. | CN |
| 40. | Cl |
| 41. | Br |
| 42. | CF₃ |
| 43. | CH₂CF₃ |
| 44. | CH₂CH₂F |
| 45. | CH₂CN |
| 46. | CH₂OCH₃ |
| 47. | CH₂OCH₂CH₃ |
| 48. | (CH₂)₂COOCH₃ |
| 49. | (CH₂)₂CONH₂ |
| 50. | (CH₂)₂CONHCH₃ |
| 51. | (CH₂)₂CON(CH₃)₂ |
| 52. | (CH₂)₂SCH₃ |
| 53. | CH₂OCH₂CH=CH₂ |
| 54. | CH₂-cycl-C₃H₅ |
| 55. | CH₂-cycl-C₆H₁₁ |
| 56. | CH=CF₂ |
| 57. | C≡C—Br |
| 58. | C≡C—OCH₃ |
| 59. | Cyclopropyl |
| 60. | Cyclobutyl |
| 61. | Cyclopentyl |
| 62. | Cyclohexyl |
| 63. | Phenyl |
| 64. | 1-Naphthyl |
| 65. | 2-Naphthyl |
| 66. | 2-F—C₆H₄ |
| 67. | 3-F—C₆H₄ |
| 68. | 4-F—C₆H₄ |
| 69. | 2,3-F₂—C₆H₃ |
| 70. | 2,4-F₂—C₆H₃ |
| 71. | 2,5-F₂—C₆H₃ |
| 72. | 2,6-F₂—C₆H₃ |
| 73. | 3,4-F₂—C₆H₃ |
| 74. | 3,5-F₂—C₆H₃ |
| 75. | 2-Cl—C₆H₄ |
| 76. | 3-Cl—C₆H₄ |
| 77. | 4-Cl—C₆H₄ |

TABLE A-continued

| No. | R₃ |
|---|---|
| 78. | 2,3-Cl₂—C₆H₃ |
| 79. | 2,4-Cl₂—C₆H₃ |
| 80. | 2,5-Cl₂—C₆H₃ |
| 81. | 2,6-Cl₂—C₆H₃ |
| 82. | 3,4-Cl₂—C₆H₃ |
| 83. | 3,5-Cl₂—C₆H₃ |
| 84. | 2,3,4-Cl₃—C₆H₂ |
| 85. | 2,3,5-Cl₃—C₆H₂ |
| 86. | 2,3,6-Cl₃—C₆H₂ |
| 87. | 2,4,5-Cl₃—C₆H₂ |
| 88. | 2,4,6-Cl₃—C₆H₂ |
| 89. | 3,4,5-Cl₃—C₆H₂ |
| 90. | 2-Br—C₆H₄ |
| 91. | 3-Br—C₆H₄ |
| 92. | 4-Br—C₆H₄ |
| 93. | 2,3-Br₂—C₆H₃ |
| 94. | 2,4-Br₂—C₆H₃ |
| 95. | 2,5-Br₂—C₆H₃ |
| 96. | 2,6-Br₂—C₆H₃ |
| 97. | 3,4-Br₂—C₆H₃ |
| 98. | 3,5-Br₂—C₆H₃ |
| 99. | 2-F-3-Cl—C₆H₃ |
| 100. | 2-F-4-Cl—C₆H₃ |
| 101. | 2-F-5-Cl—C₆H₃ |
| 102. | 2-F-3-Br—C₆H₃ |
| 103. | 2-F-4-Br—C₆H₃ |
| 104. | 2-F-5-Br—C₆H₃ |
| 105. | 2-Cl-3-Br—C₆H₃ |
| 106. | 2-Cl-3-Br—C₆H₃ |
| 107. | 2-Cl-5-Br—C₆H₃ |
| 108. | 3-F-4-Cl—C₆H₃ |
| 109. | 3-F-5-Cl—C₆H₃ |
| 110. | 3-F-6-Cl—C₆H₃ |
| 111. | 3-F-4-Br—C₆H₃ |
| 112. | 3-F-5-Br—C₆H₃ |
| 113. | 3-F-6-Br—C₆H₃ |
| 114. | 3-Cl-4-Br—C₆H₃ |
| 115. | 3-Cl-5-Br—C₆H₃ |
| 116. | 3-Cl-6-Br—C₆H₃ |
| 117. | 4-F-5-Cl—C₆H₃ |
| 118. | 4-F-6-Cl—C₆H₃ |
| 119. | 4-F-5-Br—C₆H₃ |
| 120. | 4-F-6-Br—C₆H₃ |
| 121. | 4-Cl-5-Br—C₆H₃ |
| 122. | 5-F-6-Cl—C₆H₃ |
| 123. | 5-F-6-Br—C₆H₃ |
| 124. | 5-Cl-6-Br—C₆H₃ |
| 125. | 3-Br-4-Cl-5-Br—C₆H₂ |
| 126. | 2-CN—C₆H₄ |
| 127. | 3-CN—C₆H₄ |
| 128. | 4-CN—C₆H₄ |
| 129. | 3-OCN—C₆H₄ |
| 130. | 4-CN—C₆H₄ |
| 131. | 2-CH₃O—C₆H₄ |
| 132. | 3-CH₃O—C₆H₄ |
| 133. | 4-CH₃O—C₆H₄ |
| 134. | 2,3-(CH₃O)₂—C₆H₃ |
| 135. | 2,4-(CH₃O)₂—C₆H₃ |
| 136. | 2,5-(CH₃O)₂—C₆H₃ |
| 137. | 3,4-(CH₃O)₂—C₆H₃ |
| 138. | 3,5-(CH₃O)₂—C₆H₃ |
| 139. | 3,4,5-(CH₃O)₃—C₆H₂ |
| 140. | 2-C₂H₅O—C₆H₄ |
| 141. | 3-C₂H₅O—C₆H₄ |
| 142. | 4-C₂H₅O—C₆H₄ |
| 143. | 2-(n-C₃H₇O)—C₆H₄ |
| 144. | 3-(n-C₃H₇O)—C₆H₄ |
| 145. | 4-(n-C₃H₇O)—C₆H₄ |
| 146. | 2-(i-C₃H₇O)—C₆H₄ |
| 147. | 3-(i-C₃H₇O)—C₆H₄ |
| 148. | 4-(i-C₃H₇O)—C₆H₄ |
| 149. | 4-(n-C₄H₉)—C₆H₄ |
| 150. | 3-(t-C₄H₉)—C₆H₄ |
| 151. | 4-(t-C₄H₉)—C₆H₄ |
| 152. | 2-Allyl-O—C₆H₄ |
| 153. | 3-Allyl-O—C₆H₄ |
| 154. | 4-Allyl-O—C₆H₄ |

TABLE A-continued

| No. | $R_3$ |
|---|---|
| 155. | 2-$CF_3$—$C_6H_4$ |
| 156. | 3-$CF_3$—$C_6H_4$ |
| 157. | 4-$CF_3$—$C_6H_4$ |
| 158. | 2-Acetyl-$C_6H_4$ |
| 159. | 3-Acetyl-$C_6H_4$ |
| 160. | 4-Acetyl-$C_6H_4$ |
| 161. | 2-Methoxycarbonyl-$C_6H_4$ |
| 162. | 3-Methoxycarbonyl-$C_6H_4$ |
| 163. | 4-Methoxycarbonyl-$C_6H_4$ |
| 164. | 2-Aminocarbonyl-$C_6H_4$ |
| 165. | 3-Aminocarbonyl-$C_6H_4$ |
| 166. | 4-Aminocarbonyl-$C_6H_4$ |
| 167. | 2-Dimethylaminocarbonyl-$C_6H_4$ |
| 168. | 3-Dimethylaminocarbonyl-$C_6H_4$ |
| 169. | 4-Dimethylaminocarbonyl-$C_6H_4$ |
| 170. | 2-(N-Methylaminocarbonyl)-$C_6H_4$ |
| 171. | 3-(N-Methylaminocarbonyl)-$C_6H_4$ |
| 172. | 4-(N-Methylaminocarbonyl)-$C_6H_4$ |
| 173. | 2-$CH_3S$—$C_6H_4$ |
| 174. | 3-$CH_3S$—$C_6H_4$ |
| 175. | 4-$CH_3S$—$C_6H_4$ |
| 176. | 2-$CH_3SO_2$—$C_6H_4$ |
| 177. | 3-$CH_3SO_2$—$C_6H_4$ |
| 178. | 4-$CH_3SO_2$—$C_6H_4$ |
| 179. | 2-$CF_3O$—$C_6H_4$ |
| 180. | 3-$CF_3O$—$C_6H_4$ |
| 181. | 4-$CF_3O$—$C_6H_4$ |
| 182. | 2-$CHF_2O$—$C_6H_4$ |
| 183. | 3-$CHF_2O$—$C_6H_4$ |
| 184. | 4-$CHF_2O$—$C_6H_4$ |
| 185. | 3-$CF_3$-4-$CF_3O$—$C_6H_3$ |
| 186. | 2-$CH_3NH$—$C_6H_4$ |
| 187. | 3-$CH_3NH$—$C_6H_4$ |
| 188. | 4-$CH_3NH$—$C_6H_4$ |
| 189. | 2-$(CH_3)_2N$—$C_6H_4$ |
| 190. | 3-$(CH_3)_2N$—$C_6H_4$ |
| 191. | 4-$(CH_3)_2N$—$C_6H_4$ |
| 192. | 2-Ethoxycarbonyl—$C_6H_4$ |
| 193. | 3-Ethoxycarbonyl—$C_6H_4$ |
| 194. | 4-Ethoxycarbonyl—$C_6H_4$ |
| 195. | 2-$CH_2FCH_2$—$C_6H_4$ |
| 196. | 3-$CH_2FCH_2$—$C_6H_4$ |
| 197. | 4-$CH_2FCH_2$—$C_6H_4$ |
| 198. | 2-$CF_3CH_2$—$C_6H_4$ |
| 199. | 3-$CF_3CH_2$—$C_6H_4$ |
| 200. | 4-$CF_3CH_2$—$C_6H_4$ |
| 201. | 2-$CHF_2CF_2$—$C_6H_4$ |
| 202. | 3-$CHF_2CF_2$—$C_6H_4$ |
| 203. | 4-$CHF_2CF_2$—$C_6H_4$ |
| 204. | 2-$CHF_2$—$C_6H_4$ |
| 205. | 3-$CHF_2$—$C_6H_4$ |
| 206. | 4-$CHF_2$—$C_6H_4$ |
| 207. | 2-$NO_2$—$C_6H_4$ |
| 208. | 3-$NO_2$—$C_6H_4$ |
| 209. | 4-$NO_2$—$C_6H_4$ |
| 210. | 2-$CH_3$—$C_6H_4$ |
| 211. | 3-$CH_3$—$C_6H_4$ |
| 212. | 4-$CH_3$—$C_6H_4$ |
| 213. | 2,3-$(CH_3)_2$—$C_6H_3$ |
| 214. | 2,4-$(CH_3)_2$—$C_6H_3$ |
| 215. | 2,5-$(CH_3)_2$—$C_6H_3$ |
| 216. | 2,6-$(CH_3)_2$—$C_6H_3$ |
| 217. | 3,4-$(CH_3)_2$—$C_6H_3$ |
| 218. | 3,5-$(CH_3)_2$—$C_6H_3$ |
| 219. | 2-$C_2H_5$—$C_6H_4$ |
| 220. | 3-$C_2H_5$—$C_6H_4$ |
| 221. | 4-$C_2H_5$—$C_6H_4$ |
| 222. | 2-i-$C_3H_7$—$C_6H_4$ |
| 223. | 3-i-$C_3H_7$—$C_6H4$ |
| 224. | 4-i-$C_3H_7$—$C_6H_4$ |
| 225. | 3-tert.-$C_4H_9$—$C_6H_4$ |
| 226. | 4-tert.-$C_4H_9$—$C_6H_4$ |
| 227. | 2-Vinyl—$C_6H_4$ |
| 228. | 3-Vinyl—$C_6H_4$ |
| 229. | 4-Vinyl—$C_6H_4$ |
| 230. | 2-Allyl-$C_6H_4$ |
| 231. | 3-Allyl-$C_6H4$ |
| 232. | 4-Allyl-$C_6H_4$ |
| 233. | 2-Propargyl-$C_6H_4$ |
| 234. | 2-Ethinyl-$C_6H_4$ |
| 235. | 3-Propargyloxy-$C_6H_4$ |
| 236. | 4-Butinyloxy-$C_6H_4$ |
| 237. | 2-$C_6H_5$—$C_6H_4$ |
| 238. | 3-$C_6H_5$—$C_6H_4$ |
| 239. | 3-$CH_3$, 5-t-$C_4H_9$—$C_6H_3$ |
| 240. | 2-F-4-$CH_3$—$C_6H_3$ |
| 241. | 2-F-5-$CH_3$—$C_6H_3$ |
| 242. | 2-$CH_3$-4-F—$C_6H_3$ |
| 243. | 2-$CH_3$-5-F—$C_6H_3$ |
| 244. | 2-$CH_3$-4-Cl—$C_6H_3$ |
| 245. | 2-F-4-$CH_3$—O—$C_6H_3$ |
| 246. | 2-F-4-$CH_3CH_2O$—$C_6H_3$ |
| 247. | 2-F-4-i-$C_3H_7$—$C_6H_3$ |
| 248. | 2-Pyridyl |
| 249. | 3-Pyridyl |
| 250. | 4-Pyridyl |
| 251. | 5-$CH_3$-Pyridin-2-yl |
| 252. | 5-Cl-Pyridin-2-yl |
| 253. | 6-Cl-Pyridin-2-yl |
| 254. | 3,5-$Cl_2$-Pyridin-2-yl |
| 255. | 6-$CH_3O$-Pyridin-2-yl |
| 256. | 6-$CH_3$-Pyridin-2-yl |
| 257. | 6-Cl-Pyridin-3-yl |
| 258. | 6-$CH_3$-Pyridin-3-yl |
| 259. | 6-$CH_3O$-Pyridin-3-yl |
| 260. | 2-Pyrimidinyl |
| 261. | 4-$CH_3O$-Pyrimidin-2-yl |
| 262. | 4-$C_2H_5O$-Pyrimidin-2-yl |
| 263. | 4-Cl-Pyrimidin-2-yl |
| 264. | 4-$CH_3$-Pyrimidin-2-yl |
| 265. | 5-$CH_3$-Pyrimidin-2-yl |
| 266. | 5-Cl-Pyrimidin-2-yl |
| 267. | 5-$CH_3O$-Pyrimidin-2-yl |
| 268. | 5-$C_2H_5O$-Pyrimidin-2-yl |
| 269. | 4-Pyrimidinyl |
| 270. | 2-Cl-Pyrimidin-4-yl |
| 271. | 2-$CH_3O$-Pyrimidin-4-yl |
| 272. | 2-$CH_3$-Pyrimidin-4-yl |
| 273. | 6-Cl-Pyrimidin-4-yl |
| 274. | 6-$CH_3$-Pyrimidin-4-yl |
| 275. | 6-$CH_3O$-Pyrimidin-4-yl |
| 276. | 5-Pyrimidinyl |
| 277. | 2-$CH_3$-Pyrimidin-5-yl |
| 278. | 2-Cl-Pyrimidin-5-yl |
| 279. | 2-$CH_3O$-Pyrimidin-5-yl |
| 280. | 2-$C_2H_5O$-Pyrimidin-5-yl |
| 281. | 2-Furyl |
| 282. | 4-$C_2H_5$-Fur-2-yl |
| 283. | 4-$CH_3$-Fur-2-yl |
| 284. | 4-Cl-Fur-2-yl |
| 285. | 4-CN-Fur-2-yl |
| 286. | 5-$CH_3$-Fur-2-yl |
| 287. | 5-Cl-Fur-2-yl |
| 288. | 5-CN-Fur-2-yl |
| 289. | 3-Furyl |
| 290. | 5-$CH_3$-Fur-3-yl |
| 291. | 5-Cl-Fur-3-yl |
| 292. | 5-CN-Fur-3-yl |
| 293. | 2-Thienyl |
| 294. | 4-$CH_3$-Thien-2-yl |
| 295. | 4-Cl-Thien-2-yl |
| 296. | 4-CN-Thien-2-yl |
| 297. | 5-$CH_3$-Thien-2-yl |
| 298. | 5-Cl-Thien-2-yl |
| 299. | 5-CN-Thien-2-yl |
| 300. | 3-Thienyl |
| 301. | 5-$CH_3$-Thien-3-yl |
| 302. | 5-Cl-Thien-3-yl |
| 303. | 5-CN-Thien-3-yl |
| 304. | 2-Oxazolyl |
| 305. | 4-$CH_3$-Oxazol-2-yl |
| 306. | 4-Cl-Oxazol-2-yl |
| 307. | 4-CN-Oxazol-2-yl |
| 308. | 5-$CH_3$-Oxazol-2-yl |

TABLE A-continued

| No. | R₃ |
|---|---|
| 309. | 5-Cl-Oxazol-2-yl |
| 310. | 5-CN-Oxazol-2-yl |
| 311. | 4-Oxazolyl |
| 312. | 2-CH₃-Oxazol-4-yl |
| 313. | 2-Cl-Oxazol-4-yl |
| 314. | 2-CN-Oxazol-4-yl |
| 315. | 5-Oxazolyl |
| 316. | 2-CH₃-Oxazol-5-yl |
| 317. | 2-Cl-Oxazol-5-yl |
| 318. | 2-CN-Oxazol-5-yl |
| 319. | 3-Isoxazolyl |
| 320. | 5-CH₃-Isoxazol-3-yl |
| 321. | 5-Cl-Isoxazol-3-yl |
| 322. | 5-CN-Isoxazol-3-yl |
| 323. | 5-Isoxazolyl |
| 324. | 3-CH₃-Isoxazol-5-yl |
| 325. | 3-Cl-Isoxazol-5-yl |
| 326. | 3-CN-Isoxazol-5-yl |
| 327. | 2-Thiazolyl |
| 328. | 4-CH₃-Thiazol-2-yl |
| 329. | 4-Cl-Thiazol-2-yl |
| 330. | 4-CN-Thiazol-2-yl |
| 331. | 5-CH₃-Thiazol-2-yl |
| 332. | 5-Cl-Thiazol-2-yl |
| 333. | 5-CN-Thiazol-2-yl |
| 334. | 4-Thiazolyl |
| 335. | 2-CH₃-Thiazol-4-yl |
| 336. | 2-Cl-Thiazol-4-yl |
| 337. | 2-CN-Thiazol-4-yl |
| 338. | 2-CH₃S-Thiazol-4-yl |
| 339. | 5-Thiazolyl |
| 340. | 2-CH₃-Thiazol-5-yl |
| 341. | 2-Cl-Thiazol-5-yl |
| 342. | 2-CN-Thiazol-5-yl |
| 343. | 3-Isothiazolyl |
| 344. | 5-CH₃-Isothiazol-3-yl |
| 345. | 5-Cl-Isothiazol-3-yl |
| 346. | 5-CN-Isothiazol-3-yl |
| 347. | 5-Isothiazolyl |
| 348. | 3-CH₃-Isothiazol-5-yl |
| 349. | 3-Cl-Isothiazol-5-yl |
| 350. | 3-CN-Isothiazol-5-yl |
| 351. | 2-Imidazolyl |
| 352. | 4-CH₃-Imidazol-2-yl |
| 353. | 4-Cl-Imidazol-2-yl |
| 354. | 4-CN-Imidazol-2-yl |
| 355. | 1-CH₃-Imidazol-2-yl |
| 356. | 1-CH₃-4-Cl-Imidazol-2-yl |
| 357. | 1,4-(CH₃)₂-Imidazol-2-yl |
| 358. | 1-CH₃-5-Cl-Imidazol-2-yl |
| 359. | 1,5-(CH₃)₂-Imidazol-2-yl |
| 360. | 4-Imidazolyl |
| 361. | 2-CH₃-Imidazol-4-yl |
| 362. | 2-Cl-Imidazol-4-yl |
| 363. | 1-CH₃-Imidazol-4-yl |
| 364. | 1,2-(CH₃)₂-Imidazol-4-yl |
| 365. | 1-CH₃-2-Cl-Imidazol-4-yl |
| 366. | 1-CH₃-Imidazol-5-yl |
| 367. | 1-CH₃—Cl-Imidazol-5-yl |
| 368. | 1,2-(CH₃)₂-Imidazol-5-yl |
| 369. | 3-Pyrazolyl |
| 370. | 5-CH₃-Pyrazol-3-yl |
| 371. | 5-Cl-Pyrazol-3-yl |
| 372. | 5-CN-Pyrazol-3-yl |
| 373. | 1-CH₃-Pyrazol-3-yl |
| 374. | 1-CH₃-4-Cl-Pyrazol-3-yl |
| 375. | 1-CH₃-5-Cl-Pyrazol-3-yl |
| 376. | 1,5-(CH₃)₂-Pyrazol-3-yl |
| 377. | 1-CH₃-Pyrazol-5-yl |
| 378. | 1-CH₃-3-Cl-Pyrazol-5-yl |
| 379. | 1,3-(CH₃)₂-Pyrazol-5-yl |
| 380. | 4-Pyrazolyl |
| 381. | 3-Cl-Pyrazol-4-yl |
| 382. | 3-CH₃-Pyrazol-4-yl |
| 383. | 1-CH₃-Pyrazol-4-yl |
| 384. | 1-CH₃-3-Cl-Pyrazol-4-yl |
| 385. | 1,3-(CH₃)₂-Pyrazol-4-yl |
| 386. | 1,3,4-Oxadiazol-5-yl |
| 387. | 2-CH₃-1,3,4-Oxadiazol-5-yl |
| 388. | 2-Cl-1,3,4-Oxadiazol-5-yl |
| 389. | 2-CF₃-1,3,4-Oxadiazol-5-yl |
| 390. | 2-i-C₃H₇-1,3,4-Oxadiazol-5-yl |
| 391. | 2-CH₃O-1,3,4-Oxadiazol-5-yl |
| 392. | 1,2,4-Oxadiazol-3-yl |
| 393. | 5-CH₃-1,2,4-Oxadiazol-3-yl |
| 394. | 5-i-C₃H₇-1,2,4-Oxadiazol-3-yl |
| 395. | 5-Cl-1,2,4-Oxadiazol-3-yl |
| 396. | 5-CF₃-1,2,4-Oxadiazol-3-yl |
| 397. | 1,2,4-Triazol-3-yl |
| 398. | 1-CH₃-1,2,4-Triazol-3-yl |
| 399. | 1-Pyrrolyl |
| 400. | 3-CH₃-Pyrrol-1-yl |
| 401. | 1-Pyrazolyl |
| 402. | 3-CH₃-Pyrazol-1-yl |
| 403. | 3-CF₃-Pyrazol-1-yl |
| 404. | 4-CH₃-Pyrazol-1-yl |
| 405. | 4-Cl-Pyrazol-1-yl |
| 406. | 4-Ethoxycarbonyl-Pyrazol-1-yl |
| 407. | 3-CH₃-4-Br-Pyrazol-1-yl |
| 408. | 1-Imidazolyl |
| 409. | 4-CH₃-Imidazol-1-yl |
| 410. | 4,5-Cl₂-Imidazol-1-yl |
| 411. | 2,4-(CH₃)₂-Imidazol-1-yl |
| 412. | 1,2,4-Triazol-1-yl |
| 413. | 1,3,4-Triazol-1-yl |
| 414. | 3,5-(CH₃)₂-1,2,4-Triazol-1-yl |
| 415. | 1-Piperidinyl |
| 416. | 1-Pyrrolidinyl |
| 417. | 1-Morpholinyl |
| 418. | 2-Δ²-Thiazolinyl |
| 419. | 5-CH₃-Δ²-Thiazolin-2-yl |
| 420. | 5,5-(CH₃)₂-Δ²-Thiazolin-2-yl |
| 421. | 4,5-(CH₃)₂-Δ²-Thiazolin-2-yl |
| 422. | 2-Δ²-Oxazolinyl |
| 423. | 4-CH₃-Δ²-Oxazolin-2-yl |
| 424. | 4,4-(CH₃)₂-Δ²-Oxazolin-2-yl |
| 425. | ![structure: 6-membered ring with S and N, methyl on C=N carbon] |
| 426. | ![structure: 6-membered ring with O and N, methyl on C=N carbon] |
| 427. | ![structure: 6-membered ring with O and N, methyl on C=N carbon and two CH₃ groups on carbon adjacent to N] |
| 428. | Cyclopropoxy |
| 429. | Cyclobutoxy |
| 430. | Cyclopentoxy |
| 431. | Cyclohexyloxy |
| 432. | Phenoxy |
| 433. | 1-Naphthyloxy |
| 434. | 2-Naphthyloxy |
| 435. | 2-F—C₆H₄O |
| 436. | 3-F—C₆H₄O |
| 437. | 4-F—C₆H₄O |
| 438. | 2,3-F₂—C₆H₃O |
| 439. | 2,4-F₂—C₆H₃O |
| 440. | 2,5-F₂—C₆H₃O |
| 441. | 2,6-F₂—C₆H₃O |
| 442. | 3,4-F₂—C₆H₃O |
| 443. | 3,5-F₂—C₆H₃O |
| 444. | 2-Cl—C₆H₄O |
| 445. | 3-Cl—C₆H₄O |
| 446. | 4-Cl—C₆H₄O |

TABLE A-continued

| No. | $R_3$ |
|---|---|
| 447. | 2,3-$Cl_2$—$C_6H_3O$ |
| 448. | 2,4-$Cl_2$—$C_6H_3O$ |
| 449. | 2,5-$Cl_2$—$C_6H_3O$ |
| 450. | 2,6-$Cl_2$—$C_6H_3O$ |
| 451. | 3,4-$Cl_2$—$C_6H_3O$ |
| 452. | 3,5-$Cl_2$—$C_6H_3O$ |
| 453. | 2,3,4-$Cl_3$—$C_6H_2O$ |
| 454. | 2,3,5-$Cl_3$—$C_6H_2O$ |
| 455. | 2,3,6-$Cl_3$—$C_6H_2O$ |
| 456. | 2,4,5-$Cl_3$—$C_6H_2O$ |
| 457. | 2,4,6-$Cl_3$—$C_6H_2O$ |
| 458. | 3,4,5-$Cl_3$—$C_6H_2O$ |
| 459. | 2-Br—$C_6H_4O$ |
| 460. | 3-Br—$C_6H_4O$ |
| 461. | 4-Br—$C_6H_4O$ |
| 462. | 2,3-$Br_2$—$C_6H_3O$ |
| 463. | 2,4-$Br_2$—$C_6H_3O$ |
| 464. | 2,5-$Br_2$—$C_6H_3O$ |
| 465. | 2,6-$Br_2$—$C_6H_3O$ |
| 466. | 3,4-$Br_2$—$C_6H_3O$ |
| 467. | 3,5-$Br_2$—$C_6H_3O$ |
| 468. | 2-F-3-Cl—$C_6H_3O$ |
| 469. | 2-F-4-Cl—$C_6H_3O$ |
| 470. | 2-F-5-Cl—$C_6H_3O$ |
| 471. | 2-F-3-Br—$C_6H_3O$ |
| 472. | 2-F-4-Br—$C_6H_3O$ |
| 473. | 2-F-5-Br—$C_6H_3O$ |
| 474. | 2-Cl-3-Br—$C_6H_3O$ |
| 475. | 2-Cl-4-Br—$C_6H_3O$ |
| 476. | 2-Cl-5-Br—$C_6H_3O$ |
| 477. | 3-F-4-Cl—$C_6H_3O$ |
| 478. | 3-F-5-Cl—$C_6H_3O$ |
| 479. | 3-F-6-Cl—$C_6H_3O$ |
| 480. | 3-F-4-Br—$C_6H_3O$ |
| 481. | 3-F-5-Br—$C_6H_3O$ |
| 482. | 3-F-6-Br—$C_6H_3O$ |
| 483. | 3-Cl-4-Br—$C_6H_3O$ |
| 484. | 3-Cl-5-Br—$C_6H_3O$ |
| 485. | 3-Cl-6-Br—$C_6H_3O$ |
| 486. | 4-F-5-Cl—$C_6H_3O$ |
| 487. | 4-F-6-Cl—$C_6H_3O$ |
| 488. | 4-F-5-Br—$C_6H_3O$ |
| 489. | 4-F-6-Br—$C_6H_3O$ |
| 490. | 4-Cl-5-Br—$C_6H_3O$ |
| 491. | 5-F-6-Cl—$C_6H_3O$ |
| 492. | 5-F-6-Br—$C_6H_3O$ |
| 493. | 5-Cl-6-Br—$C_6H_3O$ |
| 494. | 3-Br-4-Cl-5-Br—$C_6H_2O$ |
| 495. | 2-CN—$C_6H_4O$ |
| 496. | 3-CN—$C_6H_4O$ |
| 497. | 4-CN—$C_6H_4O$ |
| 498. | 4-Dimethylaminocarbonyl-$C_6H_4O$ |
| 499. | 2-(N-Methylaminocarbonyl)-$C_6H_4O$ |
| 500. | 3-(N-Methylaminocarbonyl)-$C_6H_4O$ |
| 501. | 4-(N-Methylaminocarbonyl)-$C_6H_4O$ |
| 502. | 2-$CH_3$S—$C_6H_4O$ |
| 503. | 3-$CH_3$S—$C_6H_4O$ |
| 504. | 4-$CH_3$S—$C_6H_4O$ |
| 505. | 2-$CH_3SO_2$—$C_6H_4O$ |
| 506. | 3-$CH_3SO_2$—$C_6H_4O$ |
| 507. | 4-$CH_3SO_2$—$C_6H_4O$ |
| 508. | 2-$CF_3O$—$C_6H_4O$ |
| 509. | 3-$CF_3O$—$C_6H_4O$ |
| 510. | 4-$CF_3O$—$C_6H_4O$ |
| 511. | 2-$CHF_2O$—$C_6H_4O$ |
| 512. | 4-$CHF_2O$—$C_6H_4O$ |
| 513. | 4-$CHF_2O$—$C_6H_4O$ |
| 514. | 3-$CF_3$, 4-$CF_3O$—$C_6H_3O$ |
| 515. | 2-$CH_3$NH—$C_6H_4O$ |
| 516. | 3-$CH_3$NH—$C_6H_4O$ |
| 517. | 4-$CH_3$NH—$C_6H_4O$ |
| 518. | 2-$(CH_3)_2$N—$C_6H_4O$ |
| 519. | 3-$(CH_3)_2$N—$C_6H_4O$ |
| 520. | 4-$(CH_3)_2$N—$C_6H_4O$ |
| 521. | 2-Ethoxycarbonyl-$C_6H_4O$ |
| 522. | 3-Ethoxycarbonyl-$C_6H_4O$ |
| 523. | 4-Ethoxycarbonyl-$C_6H_4O$ |
| 524. | 2-$CH_2FCH_2$—$C_6H_4O$ |
| 525. | 3-$CH_2FCH_2$—$C_6H_4O$ |
| 526. | 4-$CH_2FCH_2$—$C_6H_4O$ |
| 527. | 2-$CF_3CH_2$—$C_6H_4O$ |
| 528. | 3-$CF_3CH_2$—$C_6H_4O$ |
| 529. | 4-$CF_3CH_2$—$C_6H_4O$ |
| 530. | 2-$CHF_2CF_2$—$C_6H_4O$ |
| 531. | 3-$CHF_2CF_2$—$C_6H_4O$ |
| 532. | 4-$CHF_2CF_2$—$C_6H_4O$ |
| 533. | 2-$CHF_2$—$C_6H_4O$ |
| 534. | 3-$CHF_2$—$C_6H_4O$ |
| 535. | 4-$CHF_2$—$C_6H_4O$ |
| 536. | 2-$CH_3O$—$C_6H_4O$ |
| 537. | 3-$CH_3O$—$C_6H_4O$ |
| 538. | 4-$CH_3O$—$C_6H_4O$ |
| 539. | 2,3-$(CH_3O)_2$—$C_6H_3O$ |
| 540. | 2,4-$(CH_3O)_2$—$C_6H_3O$ |
| 541. | 2,5-$(CH_3O)_2$—$C_6H_3O$ |
| 542. | 3,4-$(CH_3O)_2$—$C_6H_3O$ |
| 543. | 3,5-$(CH_3O)_2$—$C_6H_3O$ |
| 544. | 3,4,5-$(CH_3O)_3$—$C_6H_2O$ |
| 545. | 2-$C_2H_5O$—$C_6H_4O$ |
| 546. | 3-$C_2H_5O$—$C_6H_4O$ |
| 547. | 4-$C_2H_5O$—$C_6H_4O$ |
| 548. | 2-(n-$C_3H_7O$)—$C_6H_4O$ |
| 549. | 3-(n-$C_3H_7O$)—$C_6H_4O$ |
| 550. | 4-(n-$C_3H_7O$)—$C_6H_4O$ |
| 551. | 2-(i-$C_3H_7O$)—$C_6H_4O$ |
| 552. | 3-(i-$C_3H_7O$)—$C_6H_4O$ |
| 553. | 4-(i-$C_3H_7O$)—$C_6H_4O$ |
| 554. | 4-(n-$C_4H_9O$)—$C_6H_4O$ |
| 555. | 3-(t-$C_4H_9O$)—$C_6H_4O$ |
| 556. | 4-(t-$C_4H_9O$)—$C_6H_4O$ |
| 557. | 2-Allyl-O—$C_6H_4O$ |
| 558. | 3-Allyl-O—$C_6H_4O$ |
| 559. | 4-Allyl-O—$C_6H_4O$ |
| 560. | 2-$CF_3$—$C_6H_4O$ |
| 561. | 3-$CF_3$—$C_6H_4O$ |
| 562. | 4-$CF_3$—$C_6H_4O$ |
| 563. | 2-Acetyl-$C_6H_4O$ |
| 564. | 3-Acetyl-$C_6H_4O$ |
| 565. | 4-Acetyl-$C_6H_4O$ |
| 566. | 2-Methoxycarbonyl-$C_6H_4O$ |
| 567. | 3-Methoxycarbonyl-$C_6H_4O$ |
| 568. | 4-Methoxycarbonyl-$C_6H_4O$ |
| 569. | 2-Aminocarbonyl-$C_6H_4O$ |
| 570. | 3-Aminocarbonyl-$C_6H_4O$ |
| 571. | 4-Aminocarbonyl-$C_6H_4O$ |
| 572. | 2-Dimethylaminocarbonyl-$C_6H_4O$ |
| 573. | 3-Dimethylaminocarbonyl-$C_6H_4O$ |
| 574. | 2-$NO_2$—$C_6H_4O$ |
| 575. | 3-$NO_2$—$C_6H_4O$ |
| 576. | 4-$NO_2$—$C_6H_4O$ |
| 577. | 2-$CH_3$—$C_6H_4O$ |
| 578. | 3-$CH_3$—$C_6H_4O$ |
| 579. | 4-$CH_3$—$C_6H_4O$ |
| 580. | 2,3-$(CH_3)_2$—$C_6H_3O$ |
| 581. | 2,4-$(CH_3)_2$—$C_6H_3O$ |
| 582. | 2,5-$(CH_3)_2$—$C_6H_3O$ |
| 583. | 2,6-$(CH_3)_2$—$C_6H_3O$ |
| 584. | 3,4-$(CH_3)_2$—$C_6H_3O$ |
| 585. | 3,5-$(CH_3)_2$—$C_6H_3O$ |
| 586. | 2-$C_2H_5$—$C_6H_3O$ |
| 587. | 3-$C_2H_5$—$C_6H_4O$ |
| 588. | 4-$C_2H_5$—$C_6H_4O$ |
| 589. | 2-i-$C_3H_7$—$C_6H_4O$ |
| 590. | 3-i-$C_3H_7$—$C_6H_4O$ |
| 591. | 4-i-$C_3H_7$—$C_6H_4O$ |
| 592. | 3-t-$C_4H_9$—$C_6H_4O$ |
| 593. | 4-t-$C_4H_9$—$C_6H_4O$ |
| 594. | 2-Vinyl-$C_6H_4O$ |
| 595. | 3-Vinyl-$C_6H_4O$ |
| 596. | 4-Vinyl-$C_6H_4O$ |
| 597. | 2-Allyl-$C_6H_4O$ |
| 598. | 3-Allyl-$C_6H_4O$ |
| 599. | 4-Allyl-$C_6H_4O$ |
| 600. | 2-$C_6H_5$—$C_6H_4O$ |

TABLE A-continued

| No. | R₃ |
|---|---|
| 601. | 3-C₆H₅—C₆H₄O |
| 602. | 4-C₆H₅—C₆H₄O |
| 603. | 3-CH₃-5-t-C₄H₉—C₆H₃O |
| 604. | 2-F-4-CH₃—C₆H₃O |
| 605. | 2-F-5-CH₃—C₆H₃O |
| 606. | 2-CH₃-4-F—C₆H₃O |
| 607. | 2-CH₃-5-F—C₆H₃O |
| 608. | 2-CH₃-4-Cl—C₆H₃O |
| 609. | 2-Pyridyloxy |
| 610. | 3-Pyridyloxy |
| 611. | 4-Pyridyloxy |
| 612. | 2-Pyrimidinyloxy |
| 613. | 4-Pyrimidinyloxy |
| 614. | 5-Pyrimidinyloxy |
| 615. | 1-CH₃-Piperidinyl-3-xy |
| 616. | 1-CH₃-Piperidinyl-4-xy |

TABLE 61

Compounds of the general formula I.7, wherein $R_5$ signifies H, $R_1$ and $R_2$ signify methyl, Q signifies O and Z corresponds in each case to one line of Table B.

I.7

Table 62
Compounds of the general formula I.7, wherein $R_5$ signifies H, $R_1$ and $R_2$ signify methyl, Q signifies OCH₂ and Z corresponds in each case to one line of Table B.

Table 63
Compounds of the general formula I.7, wherein $R_5$ signifies H, $R_1$ and $R_2$ signify methyl, Q signifies CH₂O and Z corresponds in each case to one line of Table B.

Table 64
Compounds of the general formula I.7, wherein $R_5$ signifies H, $R_1$ and $R_2$ signify methyl, Q signifies S and Z corresponds in each case to one line of Table B.

Table 65
Compounds of the general formula I.7, wherein $R_5$ signifies H, $R_1$ and $R_2$ signify methyl, Q signifies —C≡C— and Z corresponds in each case to one line of Table B.

Table 66
Compounds of the general formula I.7, wherein $R_5$ signifies H, $R_1$ and $R_2$ signify methyl, Q signifies —CH=CH— and Z corresponds in each case to one line of Table B.

Table 67
Compounds of the general formula I.7, wherein $R_5$ signifies H, $R_1$ and $R_2$ signify methyl, Q signifies —CH₂—CH₂— and Z corresponds in each case to one line of Table B.

Table 68
Compounds of the general formula I.7, wherein $R_5$ signifies H, $R_1$ and $R_2$ signify methyl, Q signifies a direct bond and Z corresponds in each case to one line of Table B.

Table 69
Compounds of the general formula I.7, wherein $R_5$ signifies H, $R_1$ signifies methyl and $R_2$ signifies ethyl, Q signifies O and Z corresponds in each case to one line of Table B.

Table 70
Compounds of the general formula I.7, wherein $R_5$ signifies H, $R_1$ signifies methyl and $R_2$ signifies ethyl, Q signifies OCH₂ and Z corresponds in each case to one line of Table B.

Table 71
Compounds of the general formula I.7, wherein $R_5$ signifies H, $R_1$ signifies methyl and $R_2$ signifies ethyl, Q signifies CH₂O and Z corresponds in each case to one line of Table B.

Table 72
Compounds of the general formula I.7, wherein $R_5$ signifies H, $R_1$ signifies methyl and $R_2$ signifies ethyl, Q signifies S and Z corresponds in each case to one line of Table B.

Table 73
Compounds of the general formula I.7, wherein $R_5$ signifies H, $R_1$ signifies methyl and $R_2$ signifies ethyl, Q signifies —C≡C— and Z corresponds in each case to one line of Table B.

Table 74
Compounds of the general formula I.7, wherein $R_5$ signifies H, $R_1$ signifies methyl and $R_2$ signifies ethyl, Q signifies —CH=CH— and Z corresponds in each case to one line of Table B.

Table 75
Compounds of the general formula I.7, wherein $R_5$ signifies H, $R_1$ signifies methyl and $R_2$ signifies ethyl, Q signifies —CH₂—CH₂— and Z corresponds in each case to one line of Table B.

Table 76
Compounds of the general formula I.7, wherein $R_5$ signifies H, $R_1$ signifies methyl and $R_2$ signifies ethyl, Q signifies a direct bond and Z corresponds in each case to one line of Table B.

Table 77
Compounds of the general formula I.7, wherein $R_5$ signifies H, $R_1$ signifies ethyl and $R_2$ signifies methyl, Q signifies O and Z corresponds in each case to one line of Table B.

Table 78
Compounds of the general formula I.7, wherein $R_5$ signifies H, $R_1$ signifies ethyl and $R_2$ signifies methyl, Q signifies OCH₂ and Z corresponds in each case to one line of Table B.

Table 79
Compounds of the general formula I.7, wherein $R_5$ signifies H, $R_1$ signifies ethyl and $R_2$ signifies methyl, Q signifies $CH_2O$ and Z corresponds in each case to one line of Table B.

Table 80
Compounds of the general formula I.7, wherein $R_5$ signifies H, $R_1$ signifies ethyl and $R_2$ signifies methyl, Q signifies S and Z corresponds in each case to one line of Table B.

Table 81
Compounds of the general formula I.7, wherein $R_5$ signifies H, $R_1$ signifies ethyl and $R_2$ signifies methyl, Q signifies —C≡C— and Z corresponds in each case to one line of Table B.

Table 82
Compounds of the general formula I.7, wherein $R_5$ signifies H, $R_1$ signifies ethyl and $R_2$ signifies methyl, Q signifies —CH=CH— and Z corresponds in each case to one line of Table B.

Table 83
Compounds of the general formula I.7, wherein $R_5$ signifies H, $R_1$ signifies ethyl and $R_2$ signifies methyl, Q signifies —$CH_2$—$CH_2$— and Z corresponds in each case to one line of Table B.

Table 84
Compounds of the general formula I.7, wherein $R_5$ signifies H, $R_1$ signifies ethyl and $R_2$ signifies methyl, Q signifies a direct bond and Z corresponds in each case to one line of Table B.

Table 85
Compounds of the general formula I.7, wherein $R_5$ signifies H, $R_1$ signifies ethyl and $R_2$ signifies ethyl, Q signifies O and Z corresponds in each case to one line of Table B.

Table 86
Compounds of the general formula I.7, wherein $R_5$ signifies H, $R_1$ signifies ethyl and $R_2$ signifies ethyl, Q signifies $OCH_2$ and Z corresponds in each case to one line of Table B.

Table 87
Compounds of the general formula I.7, wherein $R_5$ signifies H, $R_1$ signifies ethyl and $R_2$ signifies ethyl, Q signifies $CH_2O$ and Z corresponds in each case to one line of Table B.

Table 88
Compounds of the general formula I.7, wherein $R_5$ signifies H, $R_1$ signifies ethyl and $R_2$ signifies ethyl, Q signifies S and Z corresponds in each case to one line of Table B.

Table 89
Compounds of the general formula I.7, wherein $R_5$ signifies H, $R_1$ signifies ethyl and $R_2$ signifies ethyl, Q signifies —C≡C— and Z corresponds in each case to one line of Table B.

Table 90
Compounds of the general formula I.7, wherein $R_5$ signifies H, $R_1$ signifies ethyl and $R_2$ signifies ethyl, Q signifies —CH=CH— and Z corresponds in each case to one line of Table B.

Table 91
Compounds of the general formula I.7, wherein $R_5$ signifies H, $R_1$ signifies ethyl and $R_2$ signifies ethyl, Q signifies —$CH_2$—$CH_2$— and Z corresponds in each case to one line of Table B.

Table 92
Compounds of the general formula I.7, wherein $R_5$ signifies H, $R_1$ signifies ethyl and $R_2$ signifies ethyl, Q signifies a direct bond and Z corresponds in each case to one line of Table B.

Table 93
Compounds of the general formula I.7, wherein $R_5$ signifies methyl, $R_1$ and $R_2$ signify methyl, Q signifies O and Z corresponds in each case to one line of Table B.

Table 94
Compounds of the general formula I.7, wherein $R_5$ signifies methyl, $R_1$ signifies ethyl and $R_2$ signifies methyl, Q signifies O and Z corresponds in each case to one line of Table B.

Table 95
Compounds of the general formula I.7, wherein $R_5$ signifies methyl, $R_1$ signifies methyl and $R_2$ signifies ethyl, Q signifies O and Z corresponds in each case to one line of Table B.

Table 96
Compounds of the general formula I.7, wherein $R_5$ signifies methyl, $R_1$ signifies ethyl and $R_2$ signifies ethyl, Q signifies O and Z corresponds in each case to one line of Table B.

Table 97
Compounds of the general formula I.7, wherein $R_5$ signifies H, $R_1$ signifies methyl and $R_2$ signifies propargyl, Q signifies O and Z corresponds in each case to one line of Table B.

Table 98
Compounds of the general formula I.7, wherein $R_5$ signifies H, $R_1$ signifies ethyl and $R_2$ signifies propargyl, Q signifies O and Z corresponds in each case to one line of Table B.

Table 99
Compounds of the general formula I.7, wherein $R_5$ signifies H, $R_1$ signifies methyl and $R_2$ signifies allyl, Q signifies O and Z corresponds in each case to one line of Table B.

Table 100
Compounds of the general formula I.7, wherein $R_5$ signifies H, $R_1$ signifies ethyl and $R_2$ signifies allyl, Q signifies O and Z corresponds in each case to one line of Table B.

Table 101
Compounds of the general formula I.7, wherein $R_5$ signifies H, $R_1$ signifies methyl and $R_2$ signifies n-propyl, Q signifies O and Z corresponds in each case to one line of Table B.

Table 102
Compounds of the general formula I.7, wherein $R_5$ signifies H, $R_1$ signifies ethyl and $R_2$ signifies n-propyl, Q signifies O and Z corresponds in each case to one line of Table B.

Table 103
Compounds of the general formula I.7, wherein $R_5$ signifies H, $R_1$ signifies methyl and $R_2$ signifies isopropyl, Q signifies O and Z corresponds in each case to one line of Table B.

Table 104
Compounds of the general formula I.7, wherein $R_5$ signifies H, $R_1$ signifies ethyl and $R_2$ signifies isopropyl, Q signifies O and Z corresponds in each case to one line of Table B.

TABLE B

| No. | Z |
| --- | --- |
| 1. | 2-F |
| 2 | 3-F |
| 3 | 4-F |
| 4 | 2-Cl |

TABLE B-continued

| No. | Z |
|---|---|
| 5 | 3-Cl |
| 6 | 4-Cl |
| 7 | 2-Br |
| 8 | 3-Br |
| 9 | 4-Br |
| 10. | 2-$CH_3$ |
| 11. | 3-$CH_3$ |
| 12. | 4-$CH_3$ |
| 13. | 2-$CH_2CH_3$ |
| 14. | 3-$CH_2CH_3$ |
| 15. | 4-$CH_2CH_3$ |
| 16. | 4-$CH(CH_3)_2$ |
| 17. | 4-$C(CH_3)_3$ |
| 18. | 2-$CF_3$ |
| 19. | 3-$CF_3$ |
| 20. | 4-$CF_3$ |
| 21. | 2-$OCF_3$ |
| 22. | 3-$OCF_3$ |
| 23. | 4-$OCF_3$ |
| 24. | 4-$SCF_3$ |
| 25. | 4-$S(=O)CF_3$ |
| 26. | 4-$S(=O)_2CF_3$ |
| 27. | 4-CN |
| 28. | 2,3-$Cl_2$ |
| 29. | 2,4-$Cl_2$ |
| 30. | 2,5-$Cl_2$ |
| 31. | 2,6-$Cl_2$ |
| 32. | 3,4-$Cl_2$ |
| 33. | 3,5-$Cl_2$ |
| 34. | 3-Cl-4-$CF_3$ |
| 35. | 4-Cl-3-$CF_3$ |
| 36. | 3-F-4-$CF_3$ |
| 37. | 4-F-3-$CF_3$ |
| 38. | 3,4-(—$OCH_2$—O—) |
| 39. | 3,4-(—$OCF_2$—O—) |
| 40. | 3,4-(—$OCF_2CF_2$—O) |
| 41. | 3,5-$(CF_3)_2$ |

Details of the physical data in the following Tables: °=m.p. in °Celsius; Number=chemical displacement of $R_5$ in $^1$H-NMR (.δ.in ppm); * isomers

TABLE 105

Compounds of formula I

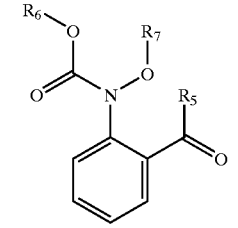

| No. | $R_1$ | $R_2$ | $R_3$ | $R_5$ | $R_6$ | $R_7$ | phys. data |
|---|---|---|---|---|---|---|---|
| 105.1 | $CH_3$ | $CH_3$ | 4-$CH_3$—$C_6H_4$ | H | $CH_3$ | $CH_3$ | 93° |
| 105.2 | $CH_3$ | $CH_3$ | 4-$CH_3CH_2$—$C_6H_4$ | H | $CH_3$ | $CH_3$ | 8.83/ 8.10 * |
| 105.3 | $CH_3$ | $CH_3$ | 4-F—$C_6H_4$ | H | $CH_3$ | $CH_3$ | 88–90° |
| 105.4 | $CH_3$ | $CH_3$ | 4-Cl—$C_6H_4$ | H | $CH_3$ | $CH_3$ | 87–90° |
| 105.5 | $CH_3$ | $CH_3$ | 4-Br—$C_6H_4$ | H | $CH_3$ | $CH_3$ | 97–98° |
| 105.6 | $CH_3$ | $CH_3$ | 4-$CH_3O$—$C_6H_4$ | H | $CH_3$ | $CH_3$ | 84–87° |
| 105.7 | $CH_3$ | $CH_3$ | 4-$CH_3CH_2O$—$C_6H_4$ | H | $CH_3$ | $CH_3$ | 115–117° |

TABLE 106

Intermediates of formula II

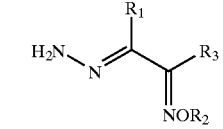

| No. | $R_1$ | $R_2$ | $R_3$ | phys. data |
|---|---|---|---|---|
| 106.1 | $CH_3$ | $CH_3$ | 4-$CH_3$—$C_6H_4$ | 112–114° |
| 106.2 | $CH_3$ | $CH_3$ | 4-$CH_3CH_2$—$C_6H_4$ | 92–95° |
| 106.3 | $CH_3$ | $CH_3$ | 4-F—$C_6H_4$ | 134–136° |
| 106.4 | $CH_3$ | $CH_3$ | 4-Cl—$C_6H_4$ | 118–119° |
| 106.5 | $CH_3$ | $CH_3$ | 4-Br—$C_6H4$ | 127–129° |
| 106.6 | $CH_3$ | $CH_3$ | 4-$CH_3O$—$C_6H_4$ | 87–90° |
| 106.7 | $CH_3$ | $CH_3$ | 4-$CH_3CH_2O$—$C_6H_4$ | 92–94° |

TABLE 107

Intermediates of formula III

| No. | $R_5$ | $R_6$ | $R_7$ | phys. data |
|---|---|---|---|---|
| 107.1 | H | $CH_3$ | $CH_3$ | 10.13 |
| 107.2 | H | $CH_3$ | $CH_3CH_2$ | |
| 107.3 | H | $CH_3CH_2$ | $CH_3$ | |
| 107.4 | H | $CH_3CH_2$ | $CH_3CH_2$ | |
| 107.5 | $CH_3$ | $CH_3$ | $CH_3$ | |
| 107.6 | $CH_3$ | $CH_3$ | $CH_3CH_2$ | |
| 107.7 | $CH_3$ | $CH_3CH_2$ | $CH_3$ | |
| 107.8 | $CH_3$ | $CH_3CH_2$ | $CH_3CH_2$ | |

Formulations may be prepared analogously to those described for example in WO 97/33890.

Biological Examples

In the following patho-systems, compounds from the tables display good activity.

A. Fungicidal Activity

EXAMPLE B-1

Activity Against *Puccinia graminis* on Wheat a) Residual Protective Action 6 days after planting, wheat plants are sprayed to drip point with an aqueous spray mixture prepared from a wettable powder of the active ingredient (0.02% active substance), and 24 hours later they are infected with a uredospore suspension of the fungus. After an incubation period of 48 hours (conditions: 95 to 100 percent relative humidity at 20°), the plants are placed in a greenhouse at 22°. 12 days after infection, the fungal attack is evaluated.

b) Systemic Action 5 days after planting, an aqueous spray mixture prepared from a wettable powder of the active ingredient (0.006% active substance, based on soil volume) is poured onto wheat plants. Care is taken that the spray mixture does not come into contact with the parts of the plants that are above ground. 48 hours later, the plants are infected with a ure-dospore suspension of the fungus. After an incubation period of 48 hours (conditions: 95 to 100 percent relative humidity at 20°), the plants are placed in a greenhouse at 22°. 12 days after infection, the fungal attack is evaluated.

EXAMPLE B-2
Activity Against *Phytophthora infestans* on Tomatoes
a) Residual Protective Action After cultivating for three weeks, tomato plants are sprayed to drip point with an aqueous spray mixture prepared from a wettable powder of the active ingredient (0.02% active substance), and 24 hours later they are infected with a sporangia suspension of the fungus. Evaluation of the fungal attack takes place 5 days after infection, during which time conditions of 90 to 100 percent relative humidity and a temperature of 20° are maintained.

b) Systemic Action

After cultivating for three weeks, an aqueous spray mixture prepared from a wettable powder of the active ingredient (0.006% active substance, based on soil volume) is poured onto tomato plants. Care is taken that the spray mixture does not come into contact with the parts of the plants that are above ground. 48 hours later, the plants are infected with a sporangia suspension of the fungus. Evaluation of the fungal attack takes place 5 days after infection, during which time conditions of 90 to 100 percent relative humidity and a temperature of 20° are maintained.

EXAMPLE B-3
Residual Protective Action Against *Cercospora arachidicola* on Peanuts Peanut plants of 10 to 15 cm height are sprayed to drip point with an aqueous spray mixture prepared from a wettable powder of the active ingredient (0.02% active substance), and 48 hours later they are infected with a conidia suspension of the fungus. The plants are incubated for 72 hours at 21° and at high atmospheric humidity, and then placed in a greenhouse until the typical leaf spots appear. Evaluation of the activity of the active substance is made 12 days after infection and is based on the number and size of leaf spots.

EXAMPLE B-4
Activity Against *Plasmopara viticola* on Grapevines

Vine seedlings at the 4 to 5 leaf stage are sprayed to drip point with an aqueous spray mixture prepared from a wettable powder of the active ingredient (0.02% active substance), and 24 hours later they are infected with a sporangia suspension of the fungus. Evaluation of the fungal attack takes place 6 days after infection, during which time conditions of 95 to 100 percent relative humidity and a temperature of 20° are maintained.

EXAMPLE B-5
Activity Against *Colletotrichum lagenarium* on Cucumbers

After cultivating for 2 weeks, cucumber plants are sprayed with an aqueous spray mixture prepared from a wettable powder of the active ingredient (concentration 0.002%). After 2 days, the plants are infected with a spore suspension ($1.5 \times 10^5$ spores/ml) of the fungus, and incubated for 36 hours at 23° C. and at high humidity. Incubation then continues at normal humidity and at ca. 22° C. The fungal attack that has set in is evaluated 8 days after infection.

EXAMPLE B-6
Residual Protective Action Against *Venturia inaequalis* on Apples Apple cuttings with new shoots of 10 to 20 cm length are sprayed to drip point with an aqueous spray mixture prepared from a wettable powder of the active ingredient (0.02% active substance), and 24 hours later they are infected with a conidia suspension of the fungus. The plants are incubated for 5 days at 90 to 100 percent relative humidity and placed in a greenhouse for a further 10 days at 20 to 24°. 12 days after infection, the fungal attack is evaluated.

EXAMPLE B-7
Activity Against *Erysiphe graminis* on Barley
a) Residual Protective Action Barley plants of approximately 8 cm height are sprayed to drip point with an aqueous spray mixture prepared from a wettable powder of the active ingredient (0.02% active substance), and 3 to 4 hours later they are dusted with conidia of the fungus. The infected plants are placed in a greenhouse at 22°. 12 days after infection, the fungal attack is evaluated.

b) Systemic Action

An aqueous spray mixture prepared from a wettable powder of the active ingredient (0.002% active substance, based on soil volume) is poured onto barley plants of approximately 8 cm height. Care is taken that the spray mixture does not come into contact with the parts of the plants that are above ground. 48 hours later, the plants are dusted with conidia of the fungus. The infected plants are placed in a greenhouse at 22°. 12 days after infection, the fungal attack is evaluated.

EXAMPLE B-8
Activity Against *Podosphaera leucotricha* on Apple Shoots

Apple cuttings with new shoots of ca. 15 cm length are sprayed with a spray mixture (0.06% active substance). After 24 hours, the treated plants are infected with a conidia suspension of the fungus and placed in a plant-growth chamber at 70% relative humidity and at 20° C. 12 days after infection, the fungal attack is evaluated.

B. Insecticidal Actvity

EXAMPLE B-9
Activity Against *Aphis craccivora*

Pea seedlings are infected with *Aphis craccivora*, subsequently sprayed with a spray mixture containing 100 ppm of active ingredient, and then incubated at 20°. The percentage reduction of the population (% response) is determined 3 and 6 days later by comparing the total number of dead aphids on the treated plants with those on the untreated plants.

EXAMPLE B-10
Activity Against *Diabrotica balteata*

Corn seedlings are sprayed with an aqueous emulsion spray mixture containing 400 ppm of active ingredient, when the spray coating has dried on they are colonised with 10 larvae of the second stage of *Diabrotica balteata* and then placed in a plastic container. The percentage reduction of the population (% response) is determined 6 days later by comparing the total number of dead larvae on the treated plants with those on the untreated plants.

EXAMPLE B-11
Activity Against *Heliothis virescens*

Young soya plants are sprayed with an aqueous emulsion spray mixture containing 100 ppm of active ingredient, when the spray coating has dried on they are colonised with 10 caterpillars of the first stage of *Heliothis virescens* and then placed in a plastic container. The percentage reduction of the population and of the feeding damage (% response) is determined 6 days later by comparing the total number of dead caterpillars and the feeding damage on the treated plants with those on the untreated plants.

EXAMPLE B-12
Activity Against *Spodoptera littoralis*

Young soya plants are sprayed with an aqueous emulsion spray mixture containing 100 ppm of active ingredient, when the spray coating has dried on they are colonised with 10 caterpillars of the third stage of *Spodoptera littoralis* and then placed in a plastic container. The percentage reduction of the population and of the feeding damage (% response) is determined 3 days later by comparing the total number of dead caterpillars and the feeding damage on the treated plants with those on the untreated plants.

EXAMPLE B-13
Activity Against *Nilaparvata lugens*

Rice plants are sprayed with an aqueous emulsion spray mixture containing 100 ppm of active ingredient. After the spray coating has dried on, the rice plants are colonised with plant and leaf-hopper larvae of the second and third stage. 21 days later they are evaluated. The percentage reduction of the population (% response) is determined by comparing the number of surviving plant and leaf-hoppers on the treated plants with those on the untreated plants.

EXAMPLE B-14
Activity Against *Plutella xylostella* Caterpillars

Young cabbage plants are sprayed with an aqueous emulsion spray mixture containing 100 ppm of active ingredient. After the spray coating has dried on, the cabbage plants are colonised with 10 caterpillars of the third stage of *Plutella xylostella* and placed in a plastic container. Three days later they are evaluated. The percentage reduction of the population and percentage reduction of feeding damage (% response) are determined by comparing the total number of dead caterpillars and the feeding damage on the treated plants with those on the untreated plants.

EXAMPLE B-15
Activity Against *Musca domestica*

A sugar cube is treated with a solution of the test compound in such a way that the concentration of test compound in the sugar, after drying over night, is 250 ppm. This treated cube is place on an aluminium dish with wet cottonwool and 10 adult *Musca domestica* of an OP-resistant strain, covered with a beaker and incubated at 25° C. The mortality rate is determined after 24 hours.

C. Acaricidal Activity

EXAMPLE B-16
Activity Against *Tetranychus urticae*

Young bean plants are colonised with a mixed population of *Tetranychus urticae* and, one day later, are sprayed one day later with an aqueous emulsion spray mixture containing 400 ppm of active ingredient. The plants are subsequently incubated for 6 days at 25 ° C. and then evaluated. The percentage reduction of the population (% response) is determined by comparing the total number of dead eggs, larvae, and adults on the treated plants with those on the untreated plants.

EXAMPLE B-17
Activity on Mixed Population of *Tetranychus cinnabarinus* Dilution Series Bush beans at the 2-leaf stage are colonised with a mixed population (eggs, larvae/nymphs, adults) of an OP-tolerant strain of *Tetranychus cinnabarinus*. 24 hours after infection, the products are applied to the plants in an automatic spray canister at dosages of 200, 100, 50 mg AS/l. The substances are ready-formulated and are diluted with water to the appropriate dosages. The test is evaluated 2 and 7 days after application by the percentage mortality of eggs, larvae/nymphs and adults. Compounds of the tables show a mortality of over 70% in dilutions up to 50 mg AS/litre.

EXAMPLE B-18
Activity Against *Boophilus microplus*

Fully engorged female adult ticks are adhered to a PVC sheet, covered with a wad of cottonwool and then 10 ml of aqueous test solution, containing 125 ppm active ingredient, is poured over them. The cottonwool is removed and the ticks are incubated for 4 weeks to lay eggs. The activity is shown either in the case of females as mortality or sterility or in the case of eggs as ovicidal activity.

We claim:
1. A compound of formula I

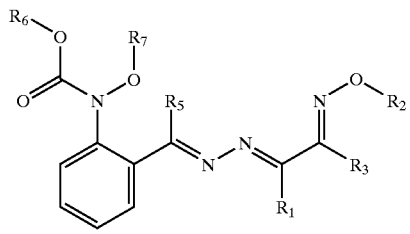

wherein
R$_1$ is C$_1$–C$_4$-alkyl or cyclopropyl;
R$_2$ is C$_1$–C$_6$-alkyl, C$_2$–C$_6$-alkenyl, C$_2$–C$_6$-alkinyl; or C$_1$–C$_6$-alkyl substituted by 1 to 5 fluorine atoms;
R$_3$ represents CN, or represents C$_1$–C$_6$-alkyl, C$_1$–C$_6$-alkoxy, C$_3$–C$_6$-cycloalkyl, C$_3$–C$_6$-cycloalkoxy, C$_2$–C$_6$-alkenyl, C$_2$–C$_6$-alkenyloxy, C$_2$–C$_6$-alkinyl, C$_2$–C$_6$-alkinyloxy, C$_1$–C$_6$-alkoxycarbonyl wherein the above-mentioned groups may be substituted by one or more identical or different substituents selected from the group comprising halogen, cyano, nitro, C$_1$–C$_6$-alkoxycarbonyl, C$_1$–C$_6$-alkoxy, C$_1$–C$_6$-alkylthio, aminocarbonyl, C$_1$–C$_6$-alkylaminocarbonyl, di-C$_1$–C$_6$-alkylaminocarbonyl, C$_2$–C$_6$-alkenyloxy, C$_3$–C$_6$-cycloalkyl, C$_3$–C$_6$-cycloalkyloxy, heterocyclyl, heterocyclyloxy, aryl, aryloxy, heteroaryl, heteroaryloxy, wherein the cyclic radicals in turn may be substituted by one or more identical or different substituents selected from the group comprising halogen, cyano, nitro, C$_1$–C$_6$-alkyl, C$_1$–C$_6$-halogenalkyl, C$_1$–C$_6$-alkoxy, C$_1$–C$_6$-halogenalkoxy, C$_1$–C$_6$-alkoxycarbonyl, C$_1$–C$_6$-alkylthio, C$_1$–C$_6$-alkylamino, di-C$_1$–C$_6$-alkylamino, C$_2$–C$_6$-alkenyl, optionally substituted benzyl, optionally substituted benzyloxy, optionally substituted aryl, optionally substituted aryloxy, optionally substituted heteroaryl and optionally substituted heteroaryloxy; wherein the above-mentioned aromatic groups may be substituted by one or more identical or different substituents selected from the group comprising halogen, cyano, nitro, C$_1$–C$_6$-alkyl, C$_1$–C$_6$-halogenalkyl, C$_1$–C$_6$-alkoxy, C$_1$–C$_6$-halogenalkoxy, C$_1$–C$_6$-alkoxycarbonyl, C$_1$–C$_6$-alkylthio, C$_1$–C$_6$-alkylamino, di-C$_1$–C$_6$-alkylamino and C$_2$–C$_6$-alkenyl; or
R$_3$ represents aryl, heteroaryl, heterocyclyl, aryloxy, heteroaryloxy or heterocyclyloxy, wherein the above-mentioned groups may be unsubstituted or substituted by one or more identical or different substituents selected from the group comprising halogen, C$_1$–C$_6$- alkyl, $C_1$–$C_6$-alkoxy, halogen-$C_1$–$C_6$-alkoxy, halogen-$C_1$–$C_6$-alkyl, $C_1$–$C_6$-alkylthio, halogen-$C_1$–$C_6$-alkylthio, $C_1$–$C_6$-alkylsulfinyl, halogen-$C_1$–$C_6$-alkylsulfinyl, $C_1$–$C_6$-alkyl-sulfonyl, halogen-$C_1$–$C_6$-alkylsulfonyl, $C_2$–$C_6$-alkenyl, $C_2$–$C_6$-alkenyloxy, $C_2$–$C_6$-alkinyl, $C_3$–$C_6$-alkinyloxy, $C_1$–$C_6$-alkylcarbonyl, halogen-$C_1$–$C_6$-alkylcarbonyl, $C_1$–$C_6$-alkoxycarbonyl, halogen-$C_1$–$C_6$-alkoxycarbonyl, $C_1$–$C_6$-alkylaminocarbonyl, di-($C_1$–$C_6$-alkyl)-aminocarbonyl, wherein the alkyl groups may be identical or different, $C_1$–$C_6$-alkylaminothiocarbonyl, di-($C_1$–$C_6$-alkyl)-aminothiocarbonyl, wherein the alkyl groups may be identical or different, $C_1$–$C_6$-alkylamino, di-($C_1$–$C_6$-alkyl)-amino, $NO_2$, an unsubstituted $C_1$–$C_4$-alkylenedioxy group or one which is mono- to tetra-substituted by $C_1$–$C_4$-alkyl and/or by halogen; or CN, $SF_5$, OH and $QR_4$;

Q represents a direct bond, O, O($C_1$–$C_6$-alkylene), ($C_1$–$C_6$-alkylene)O, S(=O)p, S(=O)p($C_1$–$C_6$-alkylene), ($C_1$–$C_6$-alkylene)S(=O)p, $C_1$–$C_8$-alkylene, $C_2$–$C_6$-alkenylene or $C_2$–$C_6$-alkinylene;

$R_4$ represents an unsubstituted $C_2$–$C_6$-alkenyl- or $C_2$–$C_6$-alkinyl group or a $C_2$–$C_6$-alkenyl- or $C_2$–$C_6$-alkinyl group which is substituted by 1 to 3 halogen atoms, or represents a ($C_1$–$C_4$-alkyl)$_3$Si group, wherein the alkyl groups may be identical or different, or represents CN, or represents an unsubstituted or mono- to pentasubstituted $C_3$–$C_6$-cycloalkyl, aryl, heteroaryl or heterocyclyl group, wherein the substituents are selected from the group comprising halogen, $C_1$–$C_6$-alkyl, halogen-$C_1$–$C_6$-alkyl, $C_1$–$C_6$-alkoxy, halogen-$C_1$–$C_6$-alkoxy, phenoxy, CN, $SF_5$, $NO_2$, $C_1$–$C_6$-alkylsulfinyl, halogen-$C_1$–$C_6$-alkylsulfinyl, $C_1$–$C_6$-alkylsulfonyl, halogen-$C_1$–$C_6$-alkylsulfonyl and $C_1$–$C_4$-alkylenedioxy, wherein the alkylenedioxy may be unsubstituted or mono- to tetrasubstituted by $C_1$–$C_4$-alkyl and/or by halogen;

p is 0, 1 or 2;

$R_5$ represents hydrogen or methyl; and $R_6$ and $R_7$ each individually represents $C_1$–$C_4$-alkyl.

2. A compound of formula I according to claim 1, wherein $R_1$ is methyl or ethyl;

$R_2$ represents methyl, ethyl, fluoromethyl or trifluoroethyl;

$R_3$ represents $C_1$–$C_6$-alkyl, $C_1$–$C_6$-alkoxy, $C_2$–$C_6$-alkenyl, $C_2$–$C_6$-alkenyloxy, $C_2$–$C_6$-alkinyl, $C_3$–$C_6$-alkinyloxy, $C_3$–$C_6$-cycloalkyl, $C_3$–$C_6$-cycloalkyloxy or $C_1$–$C_6$-alkoxycarbonyl, wherein the above-mentioned groups may be partly or wholly halogenated; furthermore CN, OCN or halogen; or phenyl which is unsubstituted or mono- to trisubstituted by identical or different substituents from halogen, $C_1$–$C_6$-alkyl, $C_1$–$C_6$-halogenalkyl, $C_1$–$C_6$-alkoxy, $C_1$–$C_6$-halogenalkoxy, $C_2$–$C_6$-alkenyl, $C_2$–$C_6$-alkenyloxy, $C_2$–$C_6$-alkinyl, $C_3$–$C_6$-alkinyloxy, $C_1$–$C_6$-alkoxycarbonyl, CN, OCN, optionally substituted benzyl, optionally substituted phenyl or optionally substituted phenoxy, wherein the above-mentioned aromatic groups may be substituted by one or more identical or different substituents selected from the group comprising halogen, cyano, nitro, $C_1$–$C_6$-alkyl, $C_1$–$C_6$-halogenalkyl, $C_1$–$C_6$-alkoxy, $C_1$–$C_6$-halogenalkoxy, $C_1$–$C_6$-alkoxycarbonyl, $C_1$–$C_6$-alkylthio, $C_1$–$C_6$-alkylamino, di-$C_1$–$C_6$-alkylamino and $C_2$–$C_6$-alkenyl; or pyridyl, pyrimidinyl, furyl, thienyl, oxazolyl, isoxazolyl, thiazolyl, isothiazolyl, imidazolyl, pyrazolyl, which are unsubstituted or mono- to trisubstituted by identical or different substituents from halogen, cyano, nitro, aminocarbonyl, $C_1$–$C_4$-alkyl, $C_1$–$C_4$-halogenalkyl, $C_1$–$C_4$-alkylcarbonyl, $C_1$–$C_4$-alkylsulfonyl, $C_1$–$C_6$-alkylsulfoxyl, $C_3$–$C_6$-cycloalkyl, optionally substituted arylcarbonyl, $C_1$–$C_4$-alkoxy, $C_1$–$C_4$-halogenalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, or $C_2$–$C_6$-alkenyl; an $R_6$ and $R_7$ each independently represent methyl or ethyl.

3. A compound of formula I according to claim 1, wherein $R_1$ is methyl or ethyl;

$R_2$ is $C_1$–$C_6$-alkyl or $C_1$–$C_6$-alkyl substituted by 1 to -5 fluorine atoms;

$R_3$ is CN, or represents unsubstituted, or partly or wholly halogenated $C_1$–$C_6$ alkyl, $C_1$–$C_6$-alkoxy, $C_1$–$C_6$-alkoxycarbonyl, $C_3$–$C_6$-cycloalkyl, or represents an aryl which is unsubstituted or mono- to trisubstituted by identical or different substituents from halogen, $C_1$–$C_6$-alkyl, $C_1$–$C_6$-halogenalkyl, $C_1$–$C_6$-alkoxy, $C_1$-$C_6$-halogenalkoxy, $C_2$–$C_6$-alkenyl, $C_2$–$C_6$-alkenyloxy, $C_2$–$C_6$-alkinyl, $C_3$–$C_6$-alkinyloxy, $C_1$–$C_6$-alkoxycarbonyl, CN, OCN, optionally substituted benzyl, optionally substituted phenyl or optionally substituted phenoxy, wherein the above-mentioned aromatic groups may be substituted by one or more identical or different substituents selected from the group comprising halogen, cyano, nitro, $C_1$–$C_6$-alkyl, $C_1$–$C_6$-halogenalkyl, $C_1$–$C_6$-alkoxy, $C_1$–$C_6$-halogenalkoxy, $C_1$–$C_6$-alkoxycarbonyl, $C_1$–$C_6$-alkylthio, $C_1$–$C_6$-alkylamino, di-$C_1$–$C_6$-alkylamino and $C_2$–$C_6$-alkenyl; or represents heteroaryl, heterocyclyl, aryloxy, heteroaryloxy or heterocyclyloxy, which are unsubstituted or mono- to trisubstituted by identical or different substituents from halogen, cyano, nitro, aminocarbonyl, $C_1$–$C_4$-alkyl, $C_1$–$C_4$-halogenalkyl, $C_1$–$C_4$-alkylcarbonyl, $C_1$–$C_4$-alkylsulfonyl, $C_1$–$C_6$-alkylsulfoxyl, $C_3$–$C_6$-cycloalkyl, optionally substituted arylcarbonyl, $C_1$–$C_4$-alkoxy, $C_1$–$C_4$-halogenalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, or $C_2$–$C_6$-alkenyl; and wherein $R_6$ and $R_7$ each individually represents methyl or ethyl.

4. A compound of formula I according to claim 1, in which $R_1$ is methyl, ethyl or cyclopropyl;

$R_2$ is $C_1$–$C_6$ alkyl;

$R_3$ is CN, or represents unsubstituted, or partly or wholly halogenated $C_1$–$C_6$-alkyl, $C_2$–$C_6$-alkenyl, $C_1$–$C_6$-alkoxy, $C_2$–$C_6$-alkenyloxy, $C_1$–$C_6$-alkoxycarbonyl, $C_3$–$C_6$-cycloalkyl, or represents an aryl which is unsubstituted or mono- to trisubstituted by identical or different substituents from halogen, $C_1$–$C_6$-alkyl, $C_1$–$C_6$-halogenalkyl, $C_1$–$C_6$-alkoxy, $C_1$–$C_6$-halogenalkoxy, $C_2$–$C_6$-alkenyl, $C_2$–$C_6$-alkenyloxy, $C_2$–$C_6$-alkinyl, $C_3$–$C_6$-alkinyloxy, $C_1$–$C_6$-alkoxycarbonyl, CN, OCN, optionally substituted benzyl, optionally substituted phenyl or optionally substituted phenoxy, wherein the above-mentioned aromatic groups may be substituted by one or more identical or different substituents selected from the group comprising halogen, cyano, nitro, $C_1$–$C_6$-alkyl, $C_1$–$C_6$-halogenalkyl, $C_1$–$C_6$-alkoxy, $C_1$–$C_6$-halogenalkoxy, $C_1$–$C_6$-alkoxycarbonyl, $C_1$–$C_6$-alkylthio, $C_1$–$C_6$-alkylamino, di-$C_1$–$C_6$- alkylamino and $C_2-C_6$-alkenyl; or represents heteroaryl, heterocyclyl, aryloxy, heteroaryloxy or heterocyclyloxy, which are unsubstituted or mono- to trisubstituted by identical or different substituents from halogen, cyano, nitro, aminocarbonyl, $C_1-C_4$-alkyl, $C_1-C_4$-halogenalkyl, $C_1-C_4$-alkylcarbonyl, $C_1-C_4$-alkylsulfonyl, $C_1-C_6$-alkylsulfoxyl, $C_3-C_6$-cycloalkyl, optionally substituted arylcarbonyl, $C_1-C_4$-alkoxy, $C_1-C_4$-halogenalkoxy, $C_1-C_6$-alkoxycarbonyl, $C_1-C_6$-alkylthio, $C_1-C_6$-alkylamino, di-$C_1-C_6$-alkylamino, $C_1-C_6$-alkylaminocarbonyl, di-$C_1-C_6$-alkylaminocarbonyl, or $C_2-C_6$-alkenyl.

5. A compound of formula I according to claim 1, wherein $R_1$ represents methyl, ethyl or cyclopropyl;

$R_2$ represents $C_1-C_6$-alkyl, $C_2-C_6$-alkenyl, or $C_2-C_6$-alkinyl, $R_3$ represents phenyl which may be substituted by one or more identical or different substituents selected from the group comprising halogen, $C_1-C_6$-alkyl, $C_1-C_6$-alkoxy, halogen-$C_1-C_6$-alkoxy, halogen-$C_1-C_6$-alkyl, $C_1-C_6$-alkylthio, halogen-$C_1-C_6$-alkylthio, $C_1-C_6$-alkylsulfinyl, halogen-$C_1-C_6$-alkylsulfinyl, $C_1-C_6$-alkyl-sulfonyl, halogen-$C_1-C_6$-alkylsulfonyl, $C_2-C_6$-alkenyl, $C_2-C_6$-alkenyloxy, $C_2-C_6$-alkinyl, $C_3-C_6$-alkinyloxy, $C_1-C_6$-alkylcarbonyl, halogen-$C_1-C_6$-alkylcarbonyl, $C_1-C_6$-alkoxycarbonyl, halogen-$C_1-C_6$-alkoxycarbonyl, $C_1-C_6$-alkylaminocarbonyl, di-($C_1-C_6$-alkyl)-aminocarbonyl, wherein the alkyl groups may be identical or different, $C_1-C_6$-alkylaminothiocarbonyl, di-($C_1-C_6$-alkyl)-aminothiocarbonyl, wherein the alkyl groups may be identical or different, $C_1-C_6$-alkylamino, di-($C_1-C_6$-alkyl)-amino, $NO_2$, an unsubstituted $C_1-C_4$-alkylenedioxy group or one which is mono- to tetrasubstituted by $C_1-C_4$-alkyl and/or by halogen; or CN, $SF_5$, OH and $QR_4$;

Q represents a direct bond, O, O($C_1-C_6$-alkylene), ($C_1-C_6$-alkylene)O, $C_1-C_6$-alkylene, $C_2-C_6$-alkenylene or $C_2-C_6$-alkinylene;

$R_4$ represents an unsubstituted or mono- to pentasubstituted $C_3-C_6$-cycloalkyl, aryl, heteroaryl or heterocyclyl group, wherein the substituents are selected from the group comprising halogen, $C_1-C_6$-alkyl, halogen-$C_1-C_6$-alkyl, $C_1-C_6$-alkoxy, halogen-$C_1-C_6$-alkoxy, phenoxy, CN, $SF_5$, $NO_2$, $C_1-C_6$-alkylsulfinyl, halogen-$C_1-C_6$-alkylsulfinyl, $C_1-C_6$-alkylsulfonyl, halogen-$C_1-C_6$-alkylsulfonyl and an unsubstituted $C_1-C_4$-alkylenedioxy or one that is mono- to tetrasubstituted by $C_1-C_4$-alkyl and/or by halogen.

6. A process for the preparation of a compound of formula I according to claim 1, comprising the step A) reacting a hydrazone of formula II

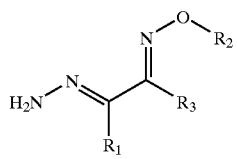

II wherein $R_1$, $R_2$ and $R_3$ are as defined in claim 1, with an aldehyde or a ketone of formula III or with one of its acetal or imino derivatives of formulae IVa and IVb

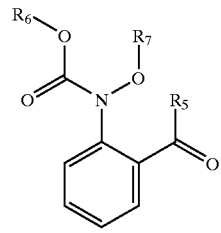

III

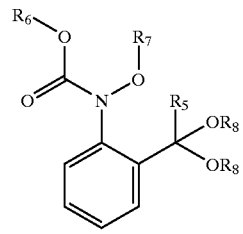

IVa

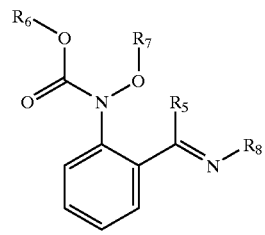

IVb wherein $R_5$, $R_6$ and $R_7$ are as defined in claim 1 and $R_8$ signifies $C_1-C_6$-alkyl or the two $R_8$, together with the two oxygen atoms and the carbon to which they are bonded, represent a cyclic acetal, or B) etherifying a N-hydroxycarbamate of formula V,

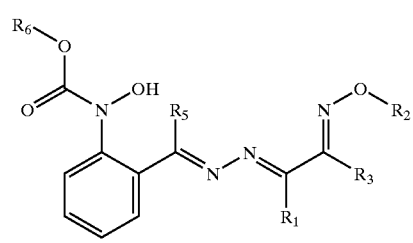

V wherein $R_1-R_3$, $R_1$ and $R_6$ are defined as for formula I.

7. A N-hydroxycarbamate of formula V,

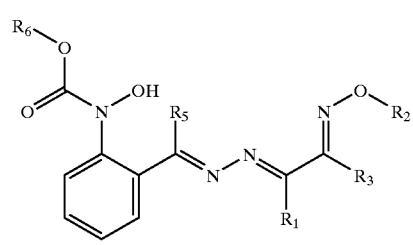

V

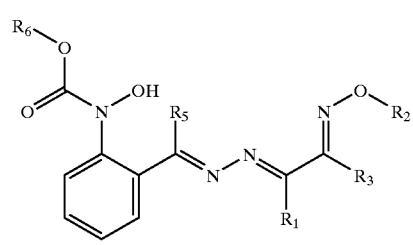

wherein $R_1-R_3$, $R_5$ and $R_6$ are defined as for formula I in claim 1.

8. A N-hydroxyaniline of the formula VI

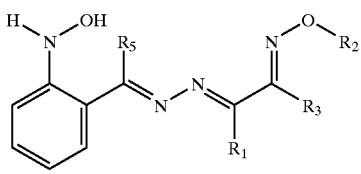

wherein $R_1$, $R_2$, $R_3$ and $R_5$ are defined as for formula I in claim 1.

9. An agrochemical composition comprising an effective quantity of
  a compound according to claim 1, and an appropriate carrier.

10. A process for the control and prevention of plant-pathogenic fungi, acarids and insects comprising the step of applying a compound according to claim 1 to plants or to their locus.

11. A compound according to claim 2, wherein $R_1$, $R_2$, $R_6$ and $R_7$ are methyl.

12. A compound according to claim 3, wherein $R_1$, $R_6$ and $R_7$ are methyl.

13. A compound according to claim 4, wherein $R_1$ is methyl and $R_2$ is methyl or ethyl.

14. A compound according to claim 5, wherein $R_2$ is methyl, ethyl, allyl or propargyl.

15. A compound according to claim 1, wherein $R_3$ represents CN, OCN or halogen, or represents unsubstituted, partially halogenated or wholly halogenated $C_1$–$C_6$-alkyl, unsubstituted, partially halogenated or wholly halogenated $C_1$–$C_6$-alkoxy, unsubstituted, partially halogenated or wholly halogenated $C_2$–$C_6$-alkenyl, unsubstituted, partially halogenated or wholly halogenated $C_2$–$C_6$-alkenyloxy, unsubstituted, partially halogenated or wholly halogenated $C_2$–$C_6$-alkinyl, unsubstituted, partially halogenated or wholly halogenated $C_3$–$C_6$-alkinyloxy, unsubstituted, partially halogenated or wholly halogenated $C_3$–$C_6$-cycloalkyl, $C_3$–$C_6$-cycloalkyloxy or unsubstituted, partially halogenated or wholly halogenated $C_1$–$C_6$-alkoxycarbonyl.

16. A compound according to claim 1, wherein $R_3$ represents phenyl which is unsubstituted or mono- to trisubstituted by identical or different substituents from halogen, $C_1$–$C_6$-alkyl, $C_1$–$C_6$-halogenalkyl, $C_1$–$C_6$-alkoxy, $C_1$–$C_6$-halogenalkoxy, $C_2$–$C_6$-alkenyl, $C_2$–$C_6$-alkenyloxy, $C_2$–$C_6$-alkinyl, $C_3$–$C_6$-alkinyloxy, $C_1$–$C_6$-alkoxycarbonyl, CN, OCN, benzyl, phenyl and phenoxy, whereby the benzyl, phenyl and phenoxy may be substituted by one or more identical or different substituents selected from the group comprising halogen, cyano, nitro, $C_1$–$C_6$-alkyl, $C_1$–$C_6$-halogenalkyl, $C_1$–$C_6$-alkoxy, $C_1$–$C_6$-halogenalkoxy, $C_1$–$C_6$-alkoxycarbonyl, $C_1$–$C_6$-alkylthio, $C_1$–$C_6$-alkylamino, di-$C_1$–$C_6$-alkylamino and $C_2$–$C_6$-alkenyl.

17. A compound according to claim 1, wherein $R_3$ represents phenyl which is substituted, preferably in 4-position, by $QR_4$, wherein Q is a direct bond, O, $OCH_2$, $CH_2O$, S, $CH_2$—$CH_2$, —CH=CH— or —C≡C—.

18. A compound according to claim 17, wherein $R_4$ represents phenyl which is unsubstituted or mono- or disubstituted by identical or different substituents from halogen, $C_1$–$C_4$-alkyl, $C_1$–$C_4$-halogenalkyl, $C_1$–$C_4$-alkoxy, $C_1$–$C_4$-halogenalkoxy, $C_2$–$C_4$-alkenyl, $C_2$–$C_4$-alkenyloxy, $C_2$–$C_4$-alkinyl, $C_3$–$C_4$-alkinyloxy, $C_1$–$C_4$-alkoxycarbonyl or CN.

19. A compound according to claim 1, wherein $R_3$ represents pyridyl, pyrimidinyl, furyl, thienyl, oxazolyl, isoxazolyl, thiazolyl, isothiazolyl, imidazolyl, pyrazolyl, which are unsubstituted or mono- to trisubstituted by identical or different substituents from halogen, cyano, nitro, aminocarbonyl, $C_1$–$C_4$-alkyl, $C_1$–$C_4$-halogenalkyl, $C_1$–$C_4$-alkylcarbonyl, $C_1$–$C_4$-alkylsulfonyl, $C_1$–$C_6$-alkylsulfoxyl, $C_3$–$C_6$-cycloalkyl, optionally substituted arylcarbonyl, $C_1$–$C_4$-alkoxy, $C_1$–$C_4$-halogenalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, or $C_2$–$C_6$-alkenyl.

20. A compound according to claim 1, wherein
  $R_3$ represents phenyl which is substituted in 4-position by $QR_4$, wherein Q is a direct bond, O, $OCH_2$, $CH_2O$, S, $CH_2$—$CH_2$, —CH=CH— or —C≡C—, and
  $R_4$ represents phenyl which is unsubstituted or mono- or disubstituted by identical or different substituents selected from halogen, $C_1$–$C_4$-alkyl, $C_1$–$C_4$-halogenalkyl, $C_1$–$C_4$-alkoxy, $C_1$–$C_4$-halogenalkoxy, $C_2$–$C_4$-alkenyl, $C_2$–$C_4$-alkenyloxy, $C_2$–$C_4$-alkinyl, $C_3$–$C_4$-alkinyloxy, $C_1$–$C_4$-alkoxycarbonyl or CN.

\* \* \* \* \*